US010226770B2

(12) United States Patent
Kimball et al.

(10) Patent No.: US 10,226,770 B2
(45) Date of Patent: Mar. 12, 2019

(54) SYSTEM FOR THERMAL CYCLING OF MICROFLUIDIC SAMPLES

(71) Applicant: Fluidigm Corporation, South San Francisco, CA (US)

(72) Inventors: Jake Kimball, Oakland, CA (US); Brandon Ripley, San Francisco, CA (US); Gang Sun, Cupertino, CA (US); Dominique Toppani, Oakland, CA (US); Myo Thu Maung, Brisband, CA (US)

(73) Assignee: Fluidigm Corporation, South San Francisco, CA (US)

( * ) Notice: Subject to any disclaimer, the term of this patent is extended or adjusted under 35 U.S.C. 154(b) by 501 days.

(21) Appl. No.: 14/864,491

(22) Filed: Sep. 24, 2015

(65) Prior Publication Data

US 2016/0114327 A1 Apr. 28, 2016

Related U.S. Application Data

(62) Division of application No. 13/429,861, filed on Mar. 26, 2012, now Pat. No. 9,168,531.
(Continued)

(51) Int. Cl.
*C12Q 3/00* (2006.01)
*B01L 7/00* (2006.01)
(Continued)

(52) U.S. Cl.
CPC ............ *B01L 7/52* (2013.01); *C12P 19/34* (2013.01); *C12Q 3/00* (2013.01); *B01L 3/5027* (2013.01);
(Continued)

(58) Field of Classification Search
None
See application file for complete search history.

(56) References Cited

U.S. PATENT DOCUMENTS

| 6,540,895 B1 | 4/2003 | Spence et al. |
| 6,762,049 B2 | 7/2004 | Zou et al. |
(Continued)

FOREIGN PATENT DOCUMENTS

| WO | 2001/067369 A2 | 9/2001 |
| WO | 2007/033385 A2 | 3/2007 |
(Continued)

OTHER PUBLICATIONS

Non-Final Office Action dated Nov. 22, 2013 for U.S. Appl. No. 13/429,861; 14 pages.
(Continued)

*Primary Examiner* — Stephanie K Mummert
(74) *Attorney, Agent, or Firm* — Kilpatrick Townsend & Stockton LLP

(57) ABSTRACT

A thermal cycler for a microfluidic device includes a controller operable to provide a series of electrical signals, a heat sink, and a heating element in thermal communication with the heat sink and operable to receive the series of electrical signals from the controller. The thermal cycler also includes a thermal chuck in thermal communication with the heating element. The thermal chuck comprises a heating surface operable to make thermal contact with the microfluidic device. The heating surface is characterized by a temperature ramp rate between 2.5 degrees Celsius per second and 5.5 degrees Celsius per second and a temperature difference between a first portion of the heating surface supporting a first portion of the microfluidic device and a second portion of the heating surface supporting a second portion of the microfluidic device is less than 0.25° C.

20 Claims, 14 Drawing Sheets

Related U.S. Application Data

(60) Provisional application No. 61/467,315, filed on Mar. 24, 2011.

(51) Int. Cl.
   *B01L 3/00* (2006.01)
   *C12P 19/34* (2006.01)
   *G01N 21/64* (2006.01)
   *G01N 21/76* (2006.01)

(52) U.S. Cl.
   CPC ... *B01L 2200/025* (2013.01); *B01L 2200/147* (2013.01); *B01L 2300/0819* (2013.01); *B01L 2300/0893* (2013.01); *B01L 2300/1805* (2013.01); *B01L 2300/1822* (2013.01); *G01N 21/6408* (2013.01); *G01N 21/6428* (2013.01); *G01N 21/6456* (2013.01); *G01N 21/76* (2013.01)

(56) References Cited

U.S. PATENT DOCUMENTS

| | | |
|---|---|---|
| 6,885,982 B2 | 4/2005 | Harris et al. |
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 2004/0180377 A1 | 9/2004 | Manger et al. |
| 2005/0053952 A1 | 3/2005 | Hong et al. |
| 2006/0172408 A1 | 8/2006 | Quake et al. |
| 2006/0233674 A1 | 10/2006 | Nelson |
| 2006/0281183 A1* | 12/2006 | Sun .................. G01N 35/0092 436/43 |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |
| 2013/0078610 A1 | 3/2013 | Kimball et al. |

FOREIGN PATENT DOCUMENTS

| | | |
|---|---|---|
| WO | 2007/044091 A2 | 4/2007 |
| WO | 2008/043046 A2 | 4/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |
| WO | 2011/053790 A2 | 5/2011 |

OTHER PUBLICATIONS

Final Office Action dated Mar. 21, 2014 for U.S. Appl. No. 13/429,861; 16 pages.
Non-Final Office Action dated Dec. 1, 2014 for U.S. Appl. No. 13/429,861; 15 pages.
Notice of Allowance dated Jun. 25, 2015 for U.S. Appl. No. 13/429,861; 5 pages.

* cited by examiner

SYSTEM FOR THERMAL CYCLING OF MICROFLUIDIC SAMPLES

CROSS-REFERENCES TO RELATED APPLICATIONS

This application is a division of U.S. application Ser. No. 13/429,861, filed Mar. 26, 2012; which claims priority to U.S. Provisional Patent Application No. 61/467,315, filed on Mar. 24, 2011. The disclosures of which are hereby incorporated by reference in their entirety for all purposes.

BACKGROUND OF THE INVENTION

To amplify DNA (Deoxyribose Nucleic Acid) using the polymerase chain reaction (PCR) process, it is necessary to cycle a specially constituted liquid reaction mixture through a PCR protocol including several different temperature incubation periods. The reaction mixture is comprised of various components such as the DNA to be amplified and at least two primers selected in a predetermined way so as to be sufficiently complementary to the sample DNA as to be able to create extension products of the DNA to be amplified. The reaction mixture includes various enzymes and/or other reagents, as well as several deoxyribonucleoside triphosphates such as dATP, dCTP, dGTP and dTTP. Generally, the primers are oligonucleotides which are capable of acting as a point of initiation of synthesis when placed under conditions in which synthesis of a primer extension product which is complimentary to a nucleic acid strand is induced, i.e., in the presence of nucleotides and inducing agents such as thermostable DNA polymerase at a suitable temperature and pH.

The Polymerase Chain Reaction (PCR) has proven a phenomenally successful technology for genetic analysis, largely because it is so simple and requires relatively low cost instrumentation. A key to PCR is the concept of thermocycling: alternating steps of melting DNA, annealing short primers to the resulting single strands, and extending those primers to make new copies of double stranded DNA. In thermocycling, the PCR reaction mixture is repeatedly cycled from high temperatures (>90° C.) for melting the DNA, to lower temperatures (40° C. to 70° C.) for primer annealing and extension. The first commercial system for performing the thermal cycling required in the polymerase chain reaction, the Perkin-Elmer Cetus DNA Thermal Cycler, was introduced in 1987.

In addition to PCR, thermal cyclers have been used in other biochemical analysis, DNA sequencing, and the like.

SUMMARY OF THE INVENTION

The present invention relates generally to biological characterization systems. More particularly, the present invention relates to methods and systems for thermal cycling samples during PCR experiments processes. Merely by way of example, the invention has been applied to a thermal cycler that provides greater thermal uniformity and a faster temperature ramp rate than conventional thermal cyclers. The methods and techniques described herein can be applied to other biological characterization systems including DNA melting assays, SNP genotyping, and the like.

According to an embodiment of the present invention, a thermal cycler for a microfluidic device is provided. The thermal cycler includes a controller operable to provide a series of electrical signal and a heat sink. The thermal cycler also includes a heating element in thermal communication with the heat sink and operable to receive the series of electrical signals from the controller and a thermal chuck in thermal communication with the heating element. The thermal chuck includes a heating surface operable to make thermal contact with the microfluidic device. The heating surface is characterized by a temperature ramp rate between 2.5 degrees Celsius per second and 5.5 degrees Celsius per second.

According to another embodiment of the present invention, a thermal cycler for a microfluidic device having a plurality of reaction chambers extending over a predetermined area in a lateral plane is provided. The thermal cycler includes a controller operable to provide a series of electrical signals and a heat sink. The thermal cycler also includes a heating element in thermal communication with the heat sink and operable to receive the series of electrical signals from the controller and a thermal chuck in thermal communication with the heating element. The thermal chuck includes a heating surface operable to make thermal contact with the microfluidic device. A temperature difference between a first portion of the heating surface supporting a first portion of the microfluidic device and a second portion of the heating surface supporting a second portion of the microfluidic device is less than 0.25° C.

According to a specific embodiment of the present invention, a method of operating a thermal cycler for a microfluidic device is provided. The thermal cycler has a heat sink, a heating element in thermal communication with the heat sink, and a thermal chuck in thermal communication with the heating element. The method includes a) providing a target temperature profile for the microfluidic device, b) determining a target temperature for the microfluidic device for increment i, and c) measuring operating temperatures. The method also includes d) computing a temperature profile for the thermal chuck and e) determining a power level for the heating element. The method further includes f) incrementing i; and g) repeating b) through f).

Numerous benefits are achieved by way of the present invention over conventional techniques. For example, embodiments of the present invention provide better temperature uniformity and a faster temperature ramp rate than conventional thermal cyclers. Moreover, embodiments of the present invention reduce the time and costs associated with performing life sciences experiments, either as a stand-alone thermal cycler or integrated with a microfluidic device. These and other embodiments of the invention along with many of its advantages and features are described in more detail in conjunction with the text below and attached figures.

DETAILED DESCRIPTION OF SPECIFIC EMBODIMENTS

Figure 1A:
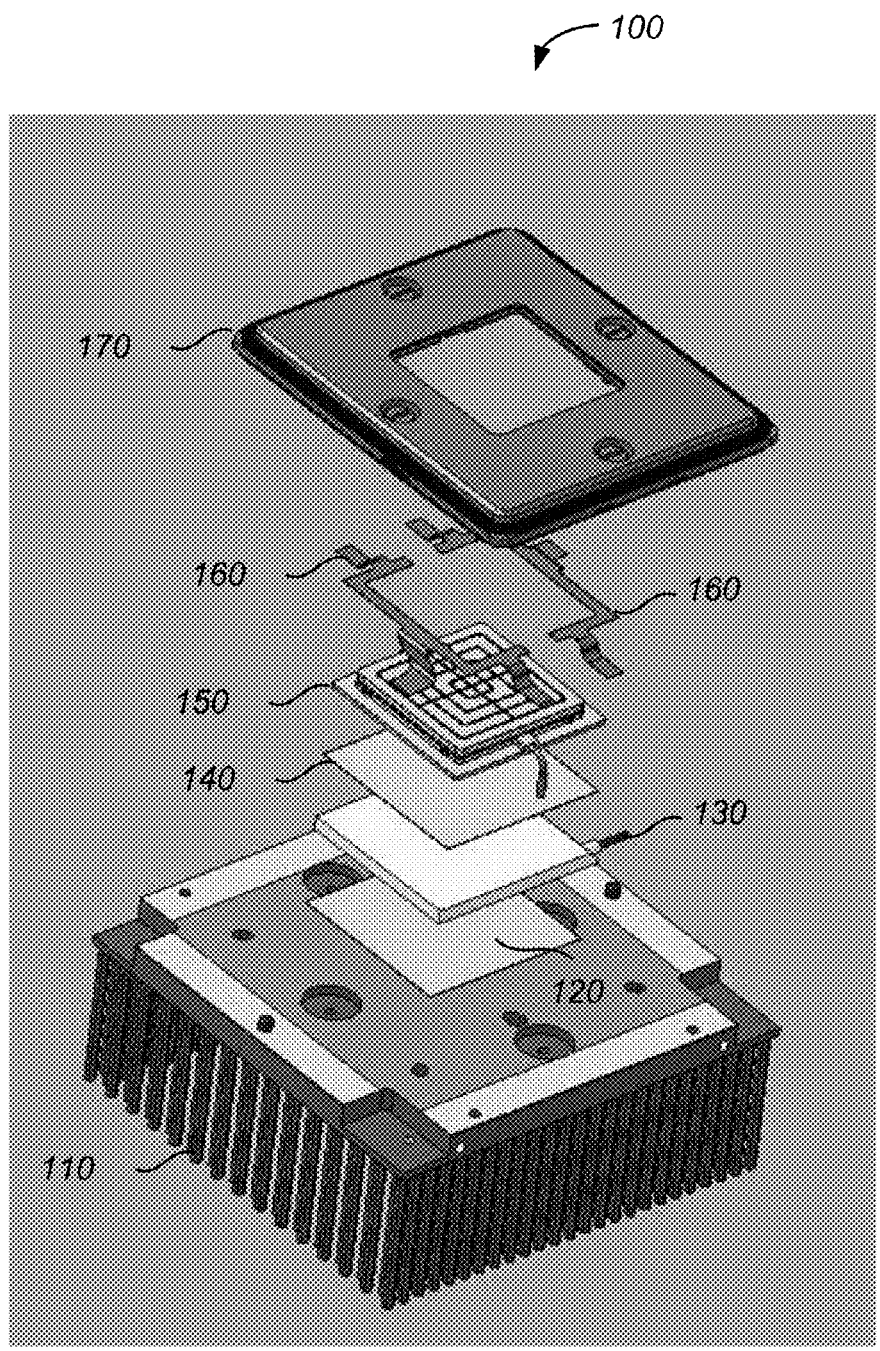
FIG. 1A is an exploded perspective view of a thermal cycler according to an embodiment of the present invention.

FIG. 1A is an exploded perspective view of a thermal cycler according to an embodiment of the present invention. The thermal cycler 100 includes a heatsink 110, a first thermal pad 120, a heating/cooling element 130, a second thermal pad 140, a thermal chuck 150, perimeter heaters 160, and a retaining ring 170. Temperature sensors (not shown) are used to monitor the temperature of the heatsink and the thermal chuck at one or more positions. In the embodiment illustrated in FIG. 1A, the thermal chuck is a vacuum chuck, although other thermal chucks are included within the scope of the present invention, including electrostatic chucks, magnetic chucks, mechanical chucks, and the like.

Figure 2A:
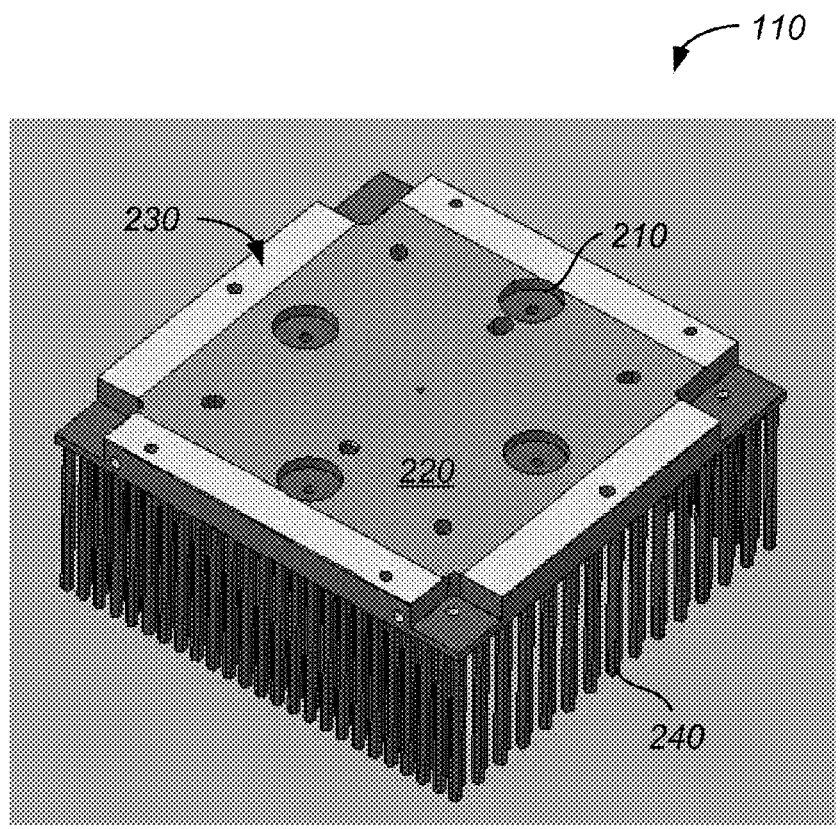
FIG. 2A is a perspective view of a heatsink according to an embodiment of the present invention.
Figure 2B:
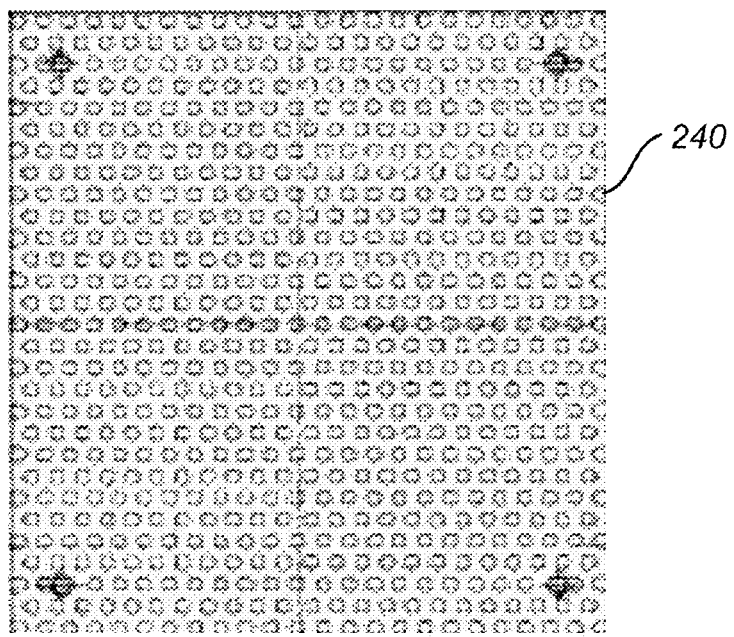
FIG. 2B is a plan view of the bottom of the heatsink illustrated in FIG. 2A according to an embodiment of the present invention.

The heatsink 110 provides for heat to be carried away from the thermal cycler in a rapid and efficient manner. FIG. 2A is a perspective view of a heatsink according to an embodiment of the present invention and FIG. 2B is a plan view of the bottom of the heatsink illustrated in FIG. 2A. Referring to FIG. 2A, four screw holes 210 are provided that are aligned with matching screw holes in the retaining ring 170 discussed below. In an alternative embodiment, the attachment mechanism between the heatsink and the retaining ring does not utilize screws, but another attachment mechanism, for example, an adhesive. In these alternative embodiments, the four screw holes illustrated in FIG. 2A are not provided.

The materials of the heatsink in the illustrated embodiment include a copper central region 220 and an aluminum outer region 230. The copper central region has a predetermined thickness as illustrated in FIG. 2A. Copper is characterized by a high thermal conductivity and therefore spreads heat uniformly across the entire heatsink. Because the heat dissipation properties of copper are limited, aluminum is used to other portions of the heatsink, for example, the outer region 230 and the radiator fins 240. The aluminum, which has good heat dissipation properties, provides a combination of materials that enable the heatsink to not only draw heat from the heating/cooling element, but also to dissipate heat quickly in order to not interfere with the cooling of the thermal cycler.

Referring to FIG. 2B, the structure of the heatsink affects the speed with which air flows into the heatsink and how well heat is dissipated. As illustrated in FIG. 2B, one embodiment of the present invention utilizes a structure including staggered row of radiator pins to provide for fast heat dissipation. In one embodiment, the radiator pins are smooth, round, and perpendicular to the base metal. Such radiator pins reduce resistance to the incoming air stream and enhance air turbulence between the radiator pins. The illustrated structure allows air to enter from all directions and also allows hot air to exit from the pin array in every horizontal direction. As a result, embodiments of the present invention enable the heatsink to dissipate heat quickly, thereby improving overall system operation cycle time. In another embodiment, the radiator pins are characterized by a cross-section that is triangular, square, hexagonal, octagonal, or another polygonal shape. Combinations of shapes can be used as a function of position as appropriate to the particular application.

As illustrated in FIG. 1A, a first thermal pad 120 is positioned between the heatsink 110 and the heating/cooling element 130. The first thermal pad facilitates the conduction of heat away from heating/cooling element to the heatsink. In addition to thermal conduction, the thermal pad provides a compliant layer, compensating for flatness variations present in the top surface of the heatsink and the bottom surface of the heating/cooling element. Thus, the thermal pad reduces or prevents the occurrence of micro-gaps between these surfaces, increasing the thermal conductivity since the thermal pad has a higher heat transfer coefficient than air. A second thermal pad 140 is placed between the heating/cooling element 130 and the thermal chuck 150.

The heating/cooling element 130 of the thermal cycler is a thermoelectric cooler (TEC) in one embodiment. A TEC serves to pump heat or draw heat away from the thermal chuck 150 based on the direction of the input current. An alternative embodiment of the heating/cooling element 130 comprises a plurality of TECs (e.g., nine TECs) arranged in a grid pattern (e.g., a 3×3 formation) to form a rectangular heating/cooling element. In an embodiment with multiple TECs, each TEC can be independently operated at different temperatures to create a predetermined temperature profile, for example uniform, graded, or the like, across the surface of the heating/cooling element. In turn, the predetermined temperature profile will result in a similar temperature profile across the face of the thermal chuck and in the microfluidic device as a result. Embodiments utilizing multiple TECs may enable the removal or a reduction in size of the perimeter heaters discussed below. Although a grid pattern is discussed above, the heating/cooling element is not limited to this particular geometry and other geometries can be utilized as appropriate to the particular application. For example, a central heating/cooling element surrounded by a set of concentric annuluses, a series of rectangular heating/cooling elements arrayed along a line, or the like, Typically, a microfluidic device is supported by the thermal chuck 150, which is a thermal source that has a thermally regulated portion that can mate with a portion of the microfluidic device, preferably the thermal conduction and distribution portion of the microfluidic device, for providing thermal control to the elastomeric block through the thermal conduction and distribution portion of the microfluidic device. In a preferred embodiment, thermal contact is improved by applying a source of vacuum to a one or more channels formed within the thermally regulated portion of the thermal chuck, wherein the channels are formed to contact a surface of the thermal conduction and distribution portion of the microfluidic device to apply suction to and maintain the position of the thermal conduction and distribution portion of the microfluidic device. In a particular embodiment, the thermal conduction and distribution portion of the microfluidic device is not in physical contact with the remainder of the microfluidic device, but is associated with the remainder of the microfluidic device and the elastomeric block by affixing the thermal conduction and distribution portion to the elastomeric block only and leaving a gap surrounding the edges of the thermal conduction and distribution portion to reduce parasitic thermal effects caused by the microfluidic device. It should be understood that in many aspects of the invention described herein, the preferred elastomeric block could be replaced with any of the known microfluidic devices in the art not described herein, for example devices produced such as the GeneChip® by Affymetrix® of Santa Clara, Calif., USA, or by Caliper of Mountain View, Calif., USA.

In some embodiments, the microfluidic device is contacted with the thermal chuck such that the thermal chuck is in thermal communication with the heating/cooling element so that a temperature of the reaction in at least one of the reaction chamber of the microfluidic device is changed as a result of a change in temperature of the heating/cooling element. Accordingly, the top surface of the vacuum chuck as illustrated in FIG. 1A not only supports a microfluidic device mounted thereon, but acts as a heating surface that can heat or cool the microfluidic device. According to an embodiment of the present invention, the thickness of the thermal chuck is approximately only half the thickness of conventional thermal chucks used in other biological analysis systems. The thin structure of the thermal chuck enables the thermal cycler to have better heat distribution and more uniformity than conventional thermal cyclers. Although a reduction in thickness by half is provided in some embodiments, other embodiments reduce the thickness even further, thereby decreasing the size of the heating/cooling element as well as the size of the heatsink. In an alternative embodiment, the thermal chuck is made out of ceramic. The life time of the system in this alternative embodiment can be extended since ceramic is more durable and is characterized by reduced expansion and stress of the system under heating.

The thermal chuck may be adapted to apply a force to the thermal transfer device to urge the thermal transfer device towards the heating/cooling element. The force may comprise a mechanical pressure, a magnetic force, an electrostatic force, an electromagnetic force, a vacuum force, other suitable forces in different embodiments. For example, in one embodiment, the force comprises a vacuum force applied towards the microfluidic device through channels formed in a surface of the thermal chuck or the microfluidic device. A level of vacuum achieved between the surface of the thermal chuck and a surface (or a portion of a surface) of the microfluidic device may be detected. Such detection may be performed with a vacuum level detector located at a position along the channel or channels distal from a location of a source of vacuum. When the vacuum does not exceed a preset level, an alert may be manifested or a realignment protocol may be engaged.

The microfluidic device may be contacted with the thermal chuck by employment of one or more mechanical or electromechanical positioning devices. Carrying out of the method may be automatically controlled and monitored. For example, such automatic control and monitoring may be performed with an automatic control system in operable communication with a robotic control system for introducing and removing the array device from the thermal chuck. The progress of the reactions may also be monitored.

A unit may be provided comprising the thermal chuck. A system may be provided comprising the microfluidic device and the thermal chuck. To ensure the accuracy of thermal cycling steps, in certain devices it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself.

Temperature can also be sensed through a change in electrical resistance. For example, change in resistance of a thermistor fabricated on an underlying semiconductor substrate utilizing conventional techniques can be calibrated to a given temperature change. Alternatively, a thermistor could be inserted directly into the microfabricated elastomer material. Still another approach to detection of temperature by resistance is described in Wu et al. in "MEMS Flow Sensors for Nano-fluidic Applications", Sensors and Actuators A 89 152-158 (2001), which is hereby incorporated by reference in its entirety. This paper describes the use of doped polysilicon structures to both control and sense temperature. For polysilicon and other semiconductor materials, the temperature coefficient of resistance can be precisely controlled by the identity and amount of dopant, thereby optimizing performance of the sensor for a given application.

Thermo-chromatic materials are another type of structure available to detect temperature on regions of an amplification device. Specifically, certain materials dramatically and reproducibly change color as they pass through different temperatures. Such a material could be added to the solution as they pass through different temperatures. Thermo-chromatic materials could be formed on the underlying substrate or incorporated within the elastomer material. Alternatively, thermo-chromatic materials could be added to the sample solution in the form of particles.

Another approach to detecting temperature is through the use of an infrared camera. An infrared camera in conjunction with a microscope could be utilized to determine the temperature profile of the entire amplification structure. Permeability of the elastomer material to radiation of appropriate wavelengths (e.g. thermal, infrared, and the like) would facilitate this analysis.

Yet another approach to temperature detection is through the use of pyroelectric sensors. Specifically, some crystalline materials, particularly those materials also exhibiting piezoelectric behavior, exhibit the pyroelectric effect. This effect describes the phenomena by which the polarization of the material's crystal lattice, and hence the voltage across the material, is highly dependent upon temperature. Such materials could be incorporated onto the substrate or elastomer and utilized to detect temperature. Other electrical phenomena, such as capacitance and inductance, can be exploited to detect temperature in accordance with embodiments of the present invention. One of ordinary skill in the art would recognize many variations, modifications, and alternatives. Additional description related to temperature measurement is found in commonly assigned U.S. Pat. No. 7,307,802, entitled "Optical Lens System and Method for Microfluidic Devices," the disclosure of which is hereby incorporated by reference in its entirety for all purposes.

Figure 3A:
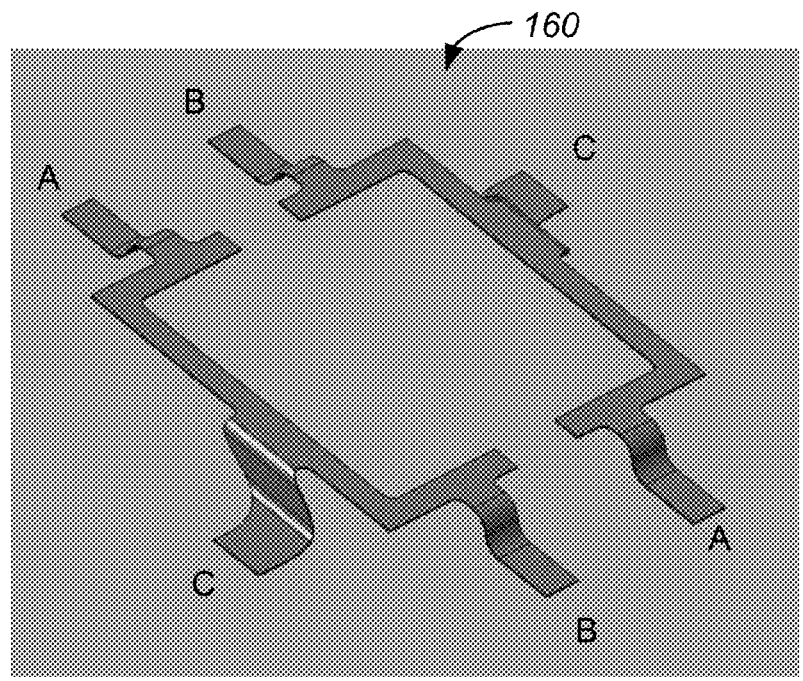
FIG. 3A is a perspective view of perimeter heaters according to an embodiment of the present invention.

Referring once again to FIG. 1A, two perimeter heaters 160 are provided at positions to the sides of the thermal chuck. FIG. 3A is a perspective view of two perimeter heaters according to an embodiment of the present invention. The perimeter heaters provide additional heat to the peripheral portions of the thermal chuck to compensate for edge effects. The perimeter heaters enable the edge and the center of the thermal chuck to be operated at a uniform temperature in embodiments for which a uniform temperature is desired. The temperature at which the perimeter heaters are operated can be based on the non-uniformity of temperature present in the microfluidic device at steady state, the thermal chuck temperature as a function of position, and the heatsink temperature in one control algorithm. As discussed above, the perimeter heaters may be reduced in size or eliminated in designs that utilize multiple heating/cooling elements.

Figure 3B:
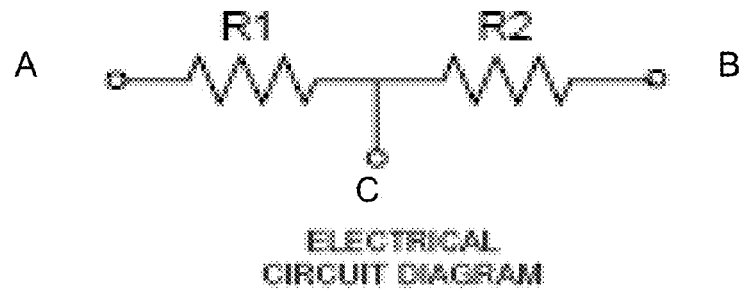
FIG. 3B is an electrical schematic of the perimeter heaters illustrated in FIG. 3A according to an embodiment of the present invention.

FIG. 3B is an electrical schematic of the perimeter heaters illustrated in FIG. 3A according to an embodiment of the present invention. Current flows from point A and point B to the ground at point C. Heat is generated as the current flow through the perimeter heaters.

Figure 4:
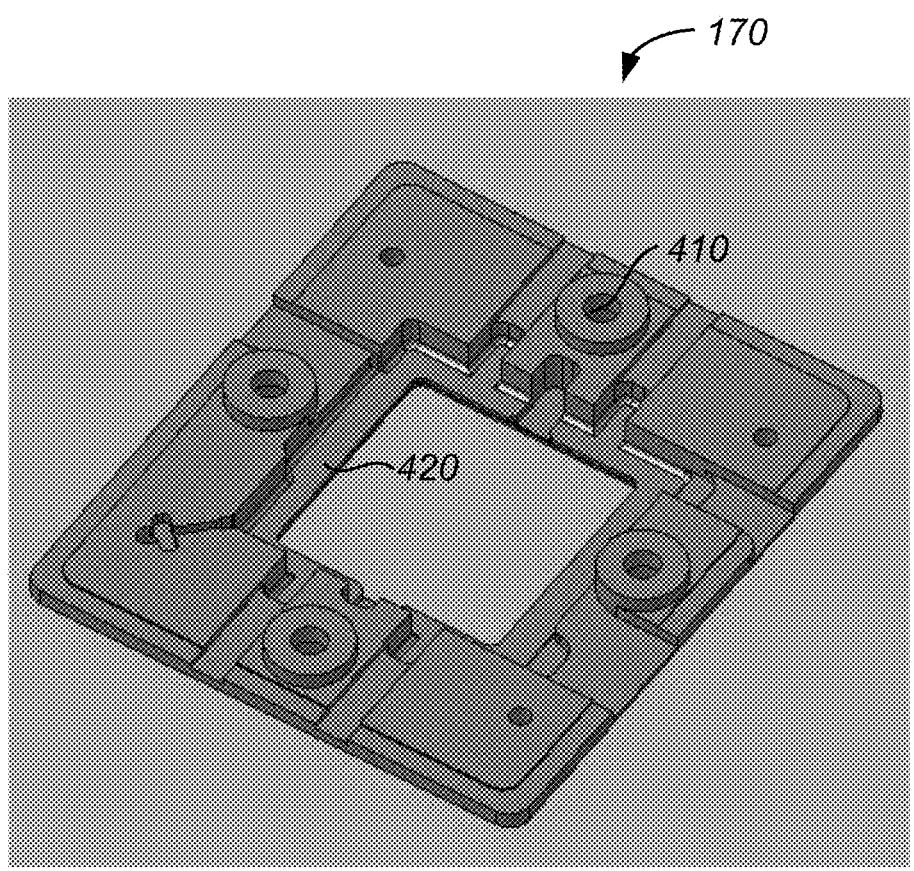
FIG. 4 is a perspective view of a retaining ring according to an embodiment of the present invention.

FIG. 4 is a perspective view of a retaining ring according to an embodiment of the present invention. The retaining ring 170 illustrated in FIG. 4 provides one mechanism for mechanically coupling the various elements of the thermal cycler, but other mechanisms are included within the scope of the present invention. The retaining ring provides mechanical force to clamp together the thermal chuck, the heating/cooling element, and the heatsink. The four holes 410 on the peripheral portions of the retaining ring align with corresponding holes on the heatsink, enabling these two members to be joined, for example, with screws. The inner portion of the retaining ring includes a raised lip 420 that overlaps with the peripheral portion (flange) of the thermal chuck 150, enabling the thermal chuck to be held securely against the second thermal pad 140 as illustrated in FIG. 1A.

In an alternative embodiment, an adhesive that is thermally conductive or heat resistant and electrically nonconductive is used in place of, or to supplement, the mechanical force provided by the retaining ring. In alternative embodiments, an adhesive, for example, EP1306 or EP1121, available from Resinlab of Germantown, Wis. or Cool-Bon, RTK7655 EG8050, ESP7455, available from AI Technology of Princeton Junction, N.J., is used to attach the thermal pads, the heating/cooling element, the heatsink, and the thermal chuck. One of ordinary skill in the art would recognize many variations, modifications, and alternatives.

Although not illustrated in FIG. 1A, embodiments of the present invention utilize a vented lid to further improve the temperature uniformity of the microfluidic device. The inventors have determined that maintaining the top surface temperature in a uniform manner reduces the gradient through the microfluidic device down to the wells and thereby improves the uniformity at the wells. The vented lid blows a small amount of air through a foam filter from directly above the microfluidic device to spread the heat from center of the microfluidic device to the edges of the microfluidic device. The foam filter diffuses the air stream to spread the air evenly onto the top of the microfluidic device.

Figure 1B:
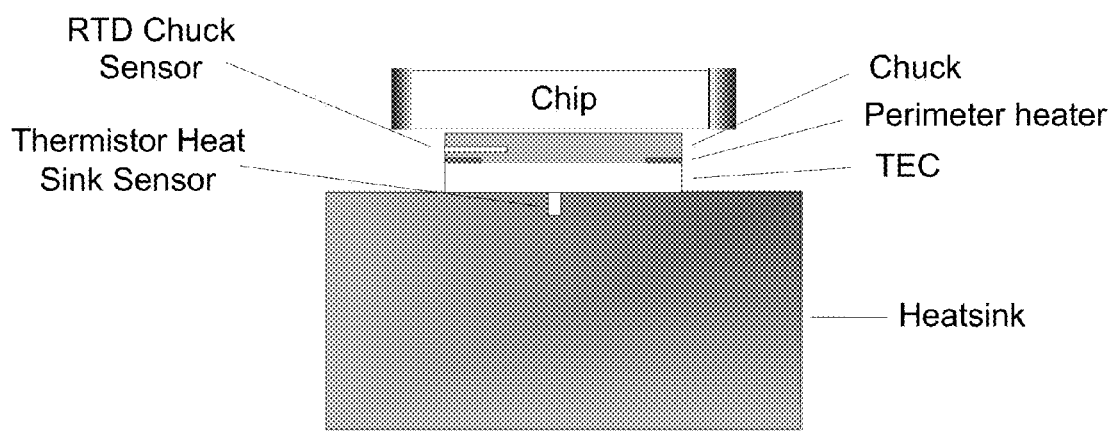
FIG. 1B is a simplified side view illustrating a thermal cycler and a microfluidic device according to an embodiment of the present invention.

FIG. 1B is a simplified side view illustrating a thermal cycler and a microfluidic device according to an embodiment of the present invention. The microfluidic device may also be referred to as a chip. The thermal cycler includes a heatsink, with a thermistor used as the heat sink sensor. The thermistor is mounted in an upper surface of the heatsink, but this is not required by the present invention. The heating/cooling element is a TEC in the embodiment illustrated in FIG. 1B and perimeter heaters are positioned at the interface of the TEC and the thermal chuck. In order to measure the temperature of the thermal chuck, an RTD sensor is mounted in the side of the thermal chuck. Other configurations for mounting a temperature sensor in the thermal chuck are also included within the scope of the present invention. In some embodiments, multiple temperature sensors (e.g., RTDs) are utilized at various portions of the thermal chuck to provide temperature measurements useful in controlling the temperature of the thermal chuck. A microfluidic device, referred to as a chip, is mounted on the thermal chuck and held in place in one embodiment by vacuum force.

Figure 5A:
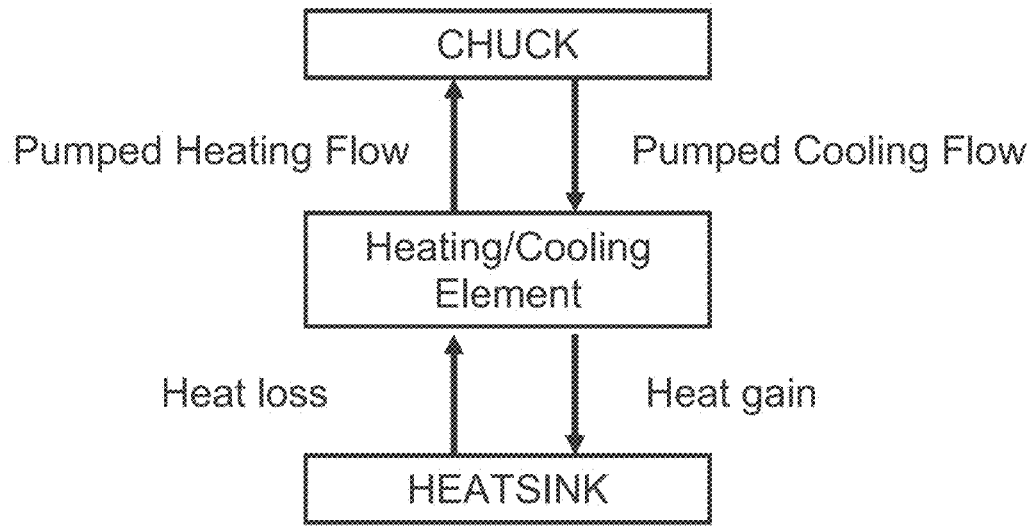
FIG. 5A is a simplified schematic diagram illustrating heat flow in the thermal cycler according to an embodiment of the present invention.

FIG. 5A is a simplified schematic diagram illustrating heat flow in the thermal cycler according to an embodiment of the present invention. The schematic illustrated in FIG. 5A may also be referred to as a thermal stack for the thermal cycler. The thermal stack includes the thermal chuck (e.g., a vacuum chuck) thermally and mechanically coupled to the heating/cooling element, which is thermally and mechanically coupled to the heatsink. The heating/cooling element pumps heat to and draw heat away from the thermal chuck. The heatsink draws heat away from the heating/cooling element.

Figure 5B:
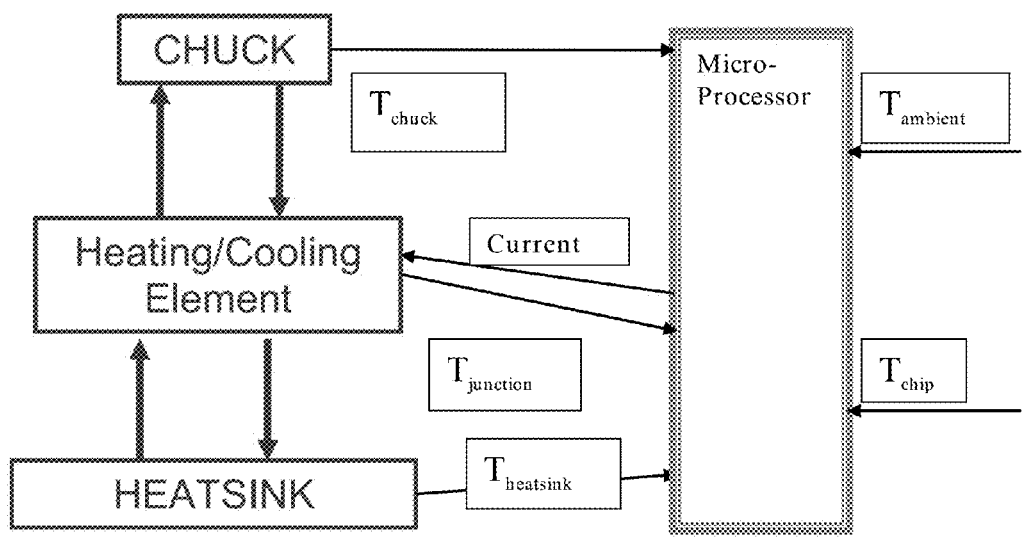
FIG. 5B is a simplified schematic diagram illustrating heat flow and temperatures in the thermal cycler according to an embodiment of the present invention.

FIG. 5B is a simplified schematic diagram illustrating heat flow and temperatures in the thermal cycler according to an embodiment of the present invention. As described more fully in relation to the thermal control algorithm discussed below, multiple temperatures are measured or computed and the temperatures are used by the algorithm that controls the heat flow and resulting temperatures of the thermal cycler. In an embodiment, the operation of the heating/cooling element depends on five different temperature measurements/computations. Referring to FIG. 5B, $T_{chuck}$ is the temperature of the thermal chuck. $T_{chuck}$ is measured using a temperature sensor, for example, a Resistance Temperature Detector (RTD) that is mounted on the inside of the thermal chuck. Other measurement devices, as described above, may also be utilized. In some embodiments, multiple temperature sensors are mounted in the thermal chuck and their contributions can be combined (e.g., averaged, a weighted average, etc.) to determine $T_{chuck}$.

$T_{junction}$ is the calculated temperature of the heating/cooling element. In an embodiment, $T_{junction}$ is computed based on the duty cycle of the signal applied to the heating/cooling element and temperature of the heatsink. $T_{heatsink}$ is the temperature of the heatsink. Typically, $T_{heatsink}$ is measured using a temperature sensor (e.g, a thermistor, RTD, or the like) integrated into the top surface of the heatsink. $T_{ambient}$ is the ambient temperature of the environment (inside of the device). $T_{ambient}$ can be measured using a temperature sensor or set at a default value, for example, 25°

C. $T_{chip}$ is a simulated temperature that is used as the target temperature for the microfluidic device. As described more fully in relation to the temperature control algorithm below, $T_{chip}$ can be computed using actual thermal chuck temperature records and measurement data (e.g, from a SensArray™ measurement device). Thus, embodiments of the present invention compute the temperature of the thermal chuck needed to reach the target temperature of the microfluidic device.

Figure 6A:
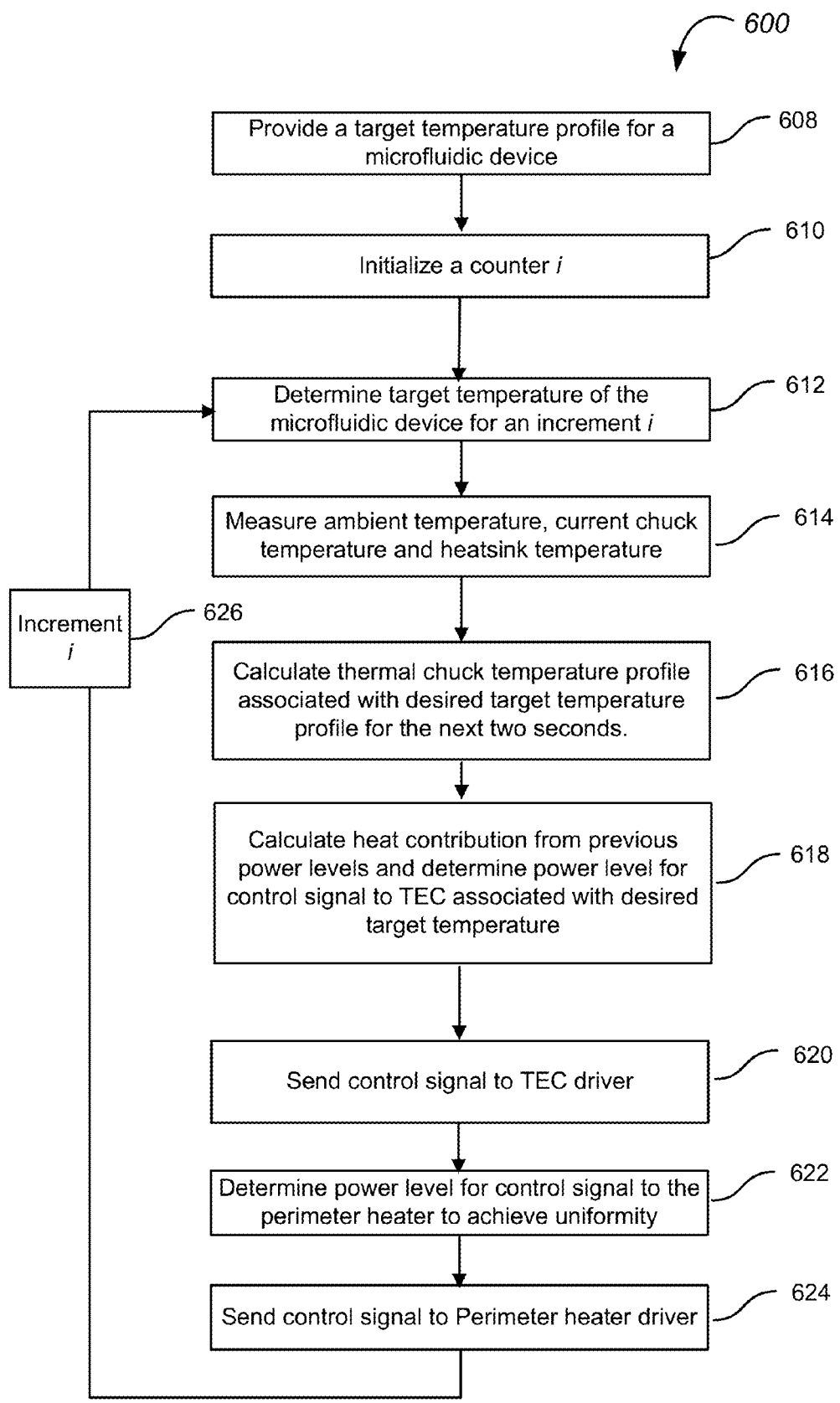
FIG. 6A is a simplified flowchart illustrating a method of operating a thermal cycler according to an embodiment of the present invention.

FIG. 6A is a simplified flowchart illustrating a method of operating a thermal cycler according to an embodiment of the present invention. As illustrated in FIG. 6A, method 600 runs a microprocessor in a control loop (on an essentially continuous basis), updating the output produced as a function of the inputs received from the temperature sensors. The method 600 includes providing a target temperature profile for a microfluidic device (608). Depending on the application and the microfluidic device, there may be multiple target temperature profiles that are stored in a library. These can also be referred to as user input heat profiles.

Figure 11A:
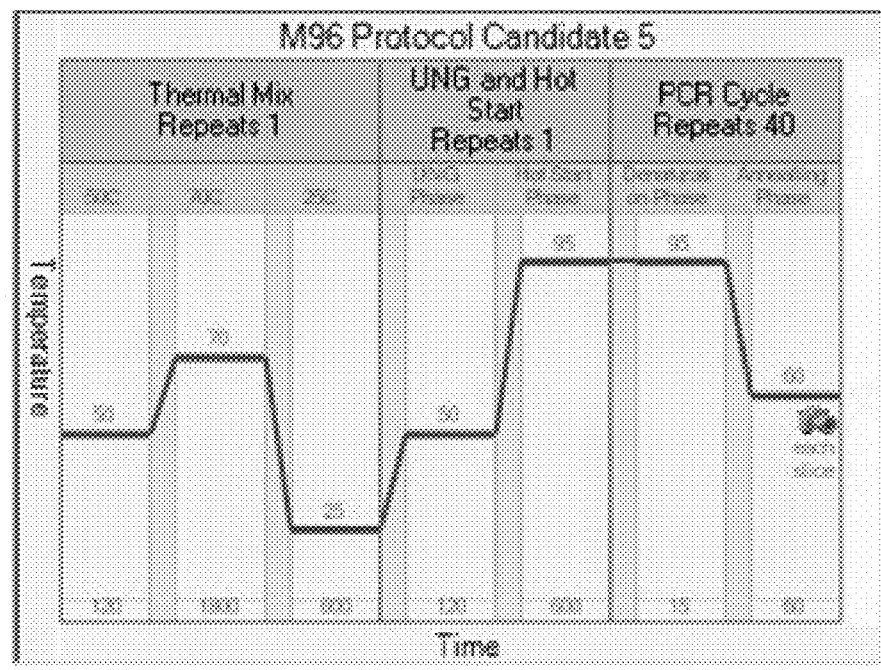
FIG. 11A illustrates a sample heating profile used for PCR according to an embodiment of the present invention.
Figure 11B:
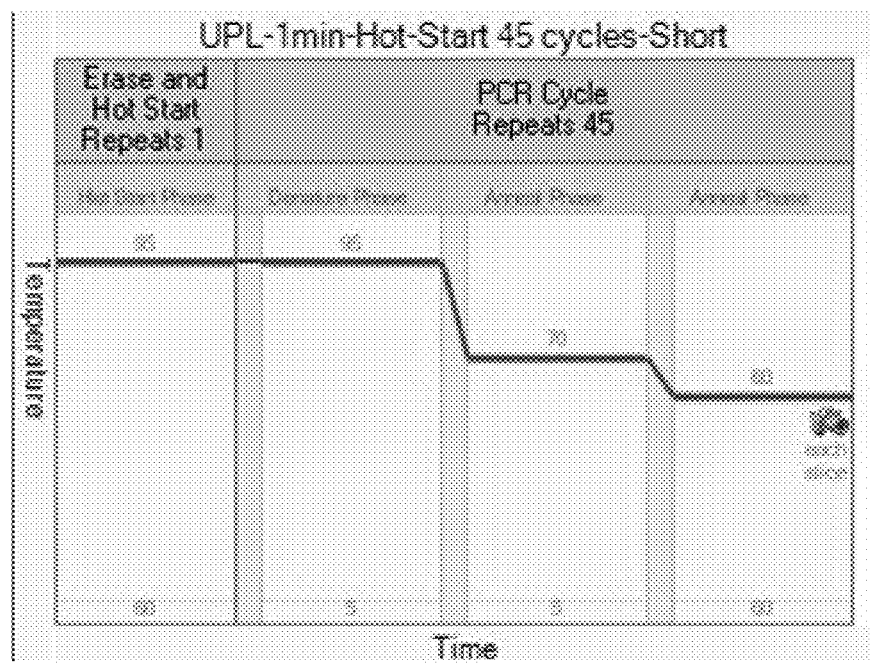
FIG. 11B illustrates a sample heating profile used for PCR according to another embodiment of the present invention.

FIGS. 11A and 11B illustrate two target temperature profiles utilized in embodiments of the present invention. The first temperature profile illustrated in FIG. 11A includes a thermal mix phase, a UNG phase, a hot start phase and a PCR phase. The thermal phase mixes the mixture within the microfluidic device uniformly; the UNG phase removes any contaminant from the previous PCR cycle; the hot start phase incubates the enzymes necessary for PCR and finally the PCR cycle amplifies DNA inside the microfluidic device. The second temperature profile includes the hot start phase and the first part of the PCR phase.

The method 600 also includes initializing a counter i (610). The counter will provide a means to divide the target temperature profile into a number of increments. In an embodiment, the number of increments is based on a cycle time of 16 Hz. Thus, for a target temperature profile 30 minutes in length, the number of increments will be 28,800 increments. Of course, other increments can be utilized according to embodiments of the present invention and operation at 16 Hz is merely used as an example of the control loop timing. One of ordinary skill in the art would recognize many variations, modifications, and alternatives.

The method additionally includes determining a target temperature for the microfluidic device for a first increment i of time (612). As an example, considering the target temperature profile illustrated in FIG. 11A, the temperature is steady from 0 to 120 seconds. The target temperature is then increased from 50° C. to 70° C. during the period between the first and second segment of the Thermal Mix phase based on the specified ramp rate. With an example ramp rate of 5.5° C./sec and an increment i of 62.5 ms, the target temperature at i=0 would be 50.00° C. and at i=1 would be 50.34° C., etc. In some embodiments, the target temperature for the increments can be considered as based on the user input heat profiles illustrated in FIGS. 11A and 11B. Temperature measurements are made for the ambient temperature ($T_{ambient}$), the thermal chuck temperature ($T_{chuck}$), and the heatsink temperature ($T_{heatsink}$) (614). In an embodiment, the RTD and the thermistor illustrated in FIG. 1B are used to measure $T_{chuck}$ and $T_{heatsink}$ and the measurements are made with the same periodicity of the increment i. In other embodiments where the temperature variation is appropriately slow, this step may be performed after several increments.

The temperature profile for the thermal chuck for the next two seconds is calculated based on the desired target temperature profile for the microfluidic device over the next two seconds (616). Although the embodiment illustrated in FIG. 6A illustrates a time period of two seconds for the calculation of the thermal chuck temperature profile and the desired target temperature profile, other time periods are included within the scope of the present invention. The temperature of the thermal chuck and the microfluidic device will be different due to a time lag during the heating/cooling process, the materials disposed between the thermal chuck and the microfluidic device, other thermal effects, and the like.

The method then calculates the heat contributions from previous power levels and uses this information to calculate the power level for the control signal associated with the desired target temperature that is to be provided to the heating/cooling element (illustrated in FIG. 6A by the TEC) (618). The control signal will result in heating or cooling of the heating/cooling element, which will drive the microfluidic device to the desired target temperature. In order to determine the power level (which can be based on amplitude of the control signal, pulse width of the control signal, or the like), a method as illustrated in FIG. 6B is utilized.

Figure 6B:
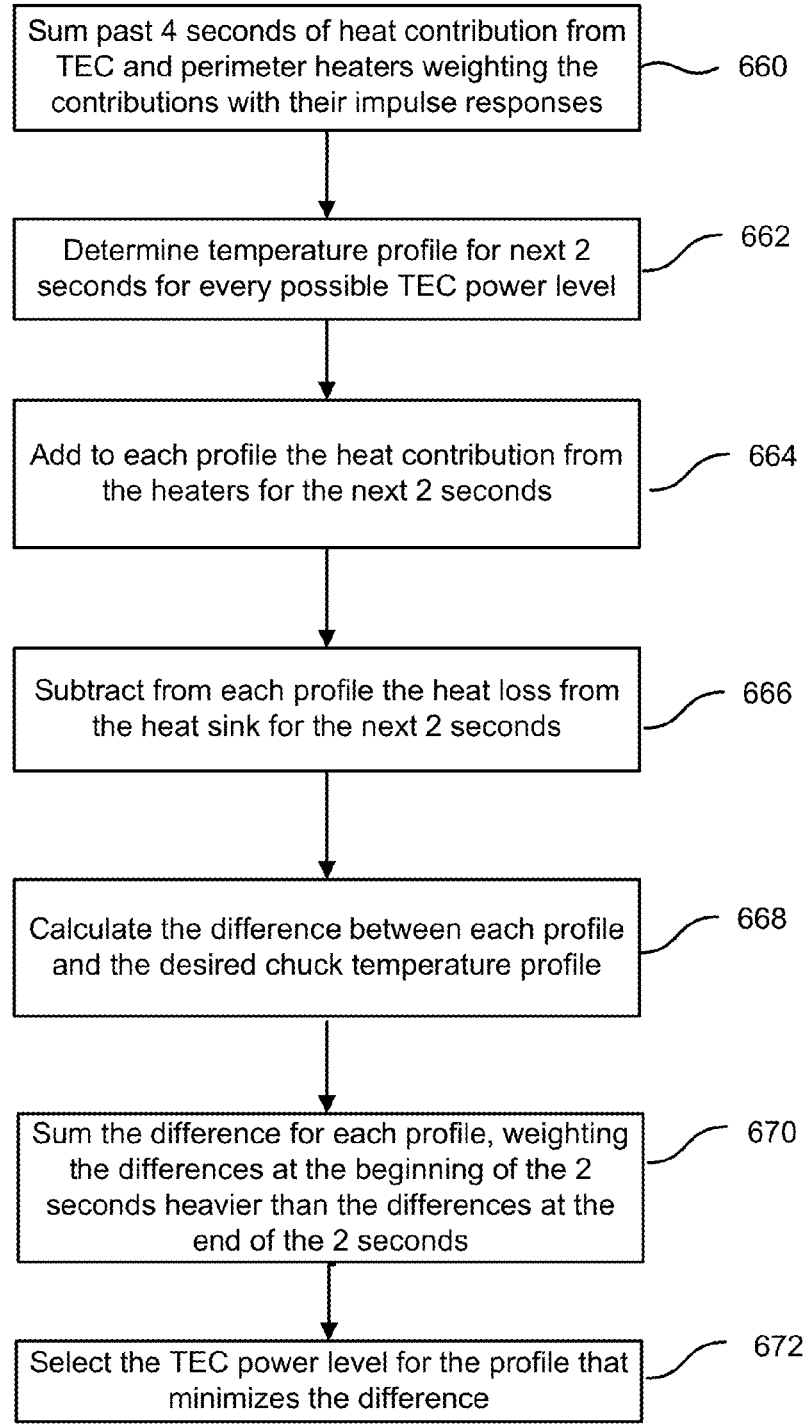
FIG. 6B is a simplified flowchart illustrating a method of determining a power level for a control signal for a heating/cooling element according to an embodiment of the present invention.

FIG. 6B is a simplified flowchart illustrating a method of calculating previous heat contribution and determining a power level for a control signal for a heating/cooling element according to an embodiment of the present invention. To determine the heat contribution from previous iterations of i, the power level applied to the TEC is analyzed as well as the power level applied to the perimeter heaters. In the case of the first iteration, the power levels from previous iterations of i are set to zero. The power levels used in step 618 extend to a predetermined time in the past, for example, for four seconds, or 64 iterations of i, resulting in 64 previous power levels. However, those 64 power level are weighted based on time. The power level from an iteration furthest away from the current iteration is given the least amount of weight when calculating the previous heat contribution, and a power level from an iteration closest to the current iteration is given the most amount of weight toward calculating the previous heat contribution. In one embodiment, the calculation of the heat contribution is based on impulse response methods utilizing experimental data in which impulse responses for various power level inputs are analyzed.

The method then determines the best power level to apply to the TEC for the next two seconds. First, it determines the temperature profile for every possible TEC power level for the next two seconds (662). Then it adds the previous calculated heat contribution to each and every temperature profile (664). Next it subtracts from each temperature profile the heat loss from the heatsink (666). Then it calculates the temperature difference between each profile and the desired chuck temperature profile (668). The method then weights the difference. The difference at the beginning of two seconds is weighted more heavily than the difference at the end of two seconds (670). Finally, the temperature profile that minimizes the difference between the temperature profile and desired chuck temperature profile is selected (672) and the corresponding TEC power level is provided as an output. Although two seconds is used in the example illustrated in FIG. 6B, this particular time period is not required by the present invention and other time periods can be utilized as appropriate to the particular application, including from sub-second time periods to time periods ranging from 1 second to 10 seconds, to time periods greater than 10 seconds. One of ordinary skill in the art would recognize many variations, modifications, and alternatives.

The calculated control signal associated with the desired target temperature is sent to the heating/cooling element driver for application to the heating/cooling element (620). Because a control signal for not only the TEC but also for the perimeter heaters is utilized in embodiments of the present invention, the power level for the control signal for use with the perimeter heaters is calculated (622). As described throughout the present specification, the perimeters heaters enable the desired temperature uniformity to be achieved. The calculated control signal associated with the perimeter heaters is sent to the perimeter heater driver for application to the perimeter heaters (624). In embodiments utilizing a multi-zone heating/cooling element, steps 616-624 can be combined into fewer or more steps as appropriate to providing control signals to the individual zones making up the heating/cooling elements.

The method 600 further includes incrementing the counter i (626) and repeating the loop defined by steps 612-624. Thus, the control loop runs continuously during the thermal cycling process in order to drive the actual temperature of the microfluidic device toward the desired temperature profile. Embodiments of the present invention provide for improvements over conventional designs since the temperature of the microfluidic device can be driven to a predetermined temperature profile, reducing overshoot and undershoot. Additionally, as described in relation to FIG. 6B, embodiments of the present invention utilize a predicative algorithm that takes into account the target temperature in the next 2 or 3 seconds. By looking ahead, the power level of the control signals is controlled to minimize overshooting and undershooting the temperature of the thermal chuck when changing temperatures. In a particular embodiment, rather than varying the amplitude of the current to the heating/cooling element to control the temperature, the power level is adjusted by varying the duty cycle of the control signal. As described above, methods of the present invention takes into account both the past and future temperature when calculating the power level for the control signal provided to the heating/cooling elements (e.g., TEC and perimeter heaters), enabling stable and smooth outputs.

Figure 7:
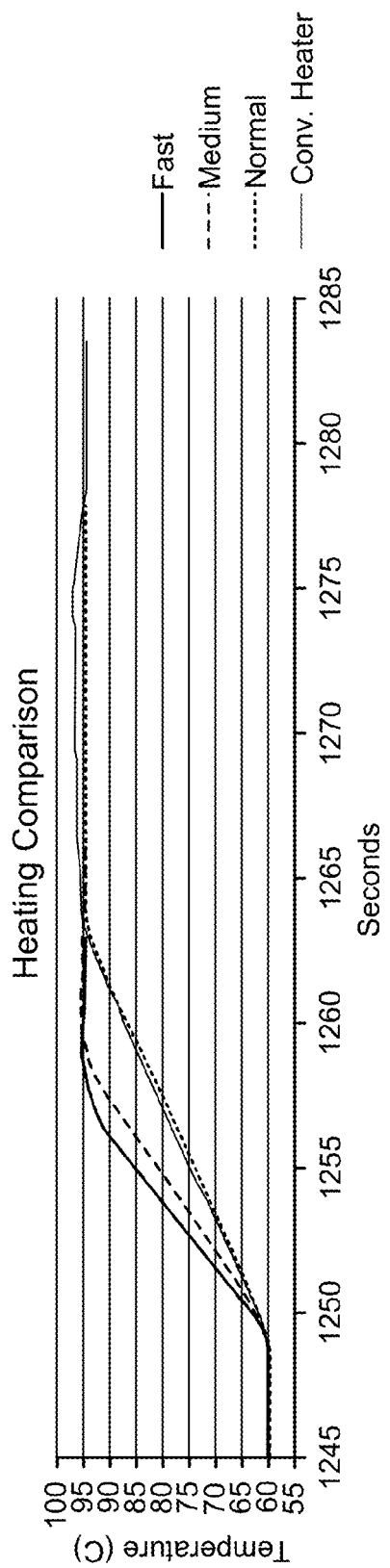
FIG. 7 is a simplified plot showing microfluidic device temperatures as a function of time for various control algorithms according to embodiments of the present invention.

FIG. 7 is a simplified plot showing microfluidic device temperatures as a function of time for various control algorithms according to embodiments of the present invention. As illustrated in FIG. 7, the temperature ramp rate of the thermal cycler is a function of the control algorithm utilized: fast, medium, or normal. It should be noted that the thermal cycler provided by embodiments of the present invention has a faster temperature ramp rate than the conventional thermal cycler for one or more of the control algorithms. As illustrated in FIG. 7, the thermal cycler is able to provide a temperature change of the 5.5° C./s from 60° C. to 95° C. in 8.5 s on the fast setting, 9.5 s on medium setting and 14 s on normal settings. The conventional thermal cycler performed the same temperature change in 13.5 s.

Figure 8A:
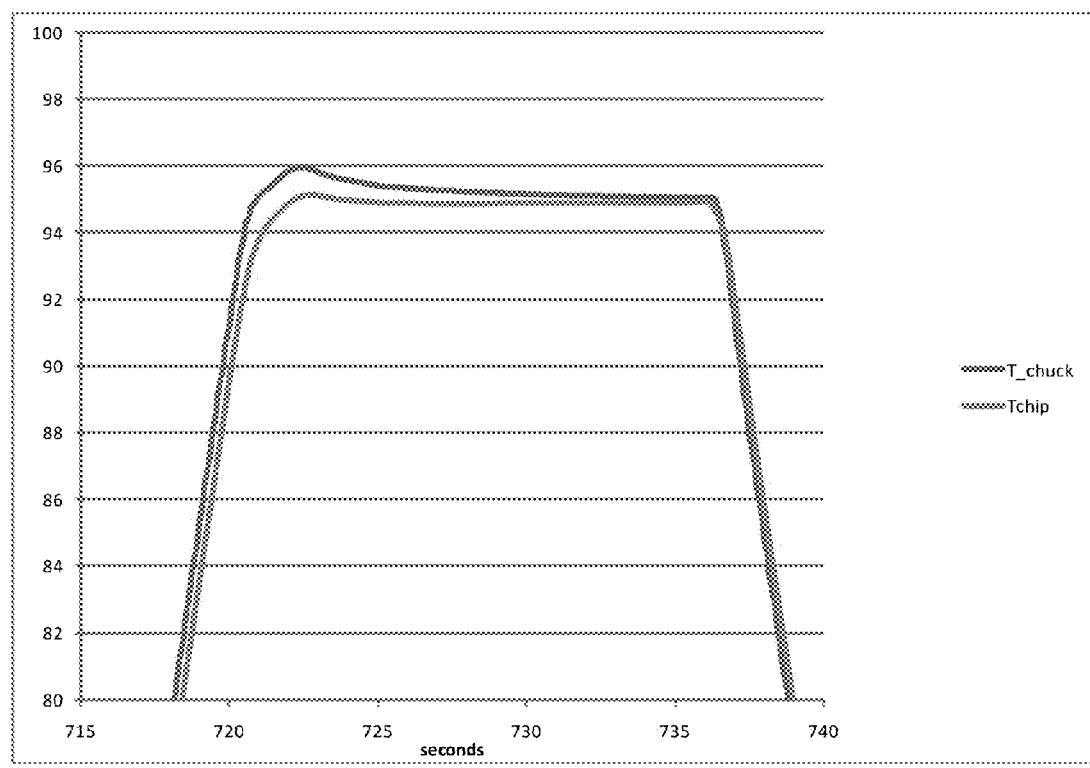
FIG. 8A is a simplified plot showing the temperature of the thermal chuck and the microfluidic device as a function of time during heating according to an embodiment of the present invention.

FIG. 8A is a simplified plot showing the temperature of the thermal chuck and the microfluidic device as a function of time during heating according to an embodiment of the present invention. As illustrated in FIG. 8A, the ramp rate of the microfluidic device temperature is on the order of 5.5° C./s, with little overshoot. The temperature rise of the thermal chuck leads the temperature rise of the microfluidic device slightly.

Figure 8B:
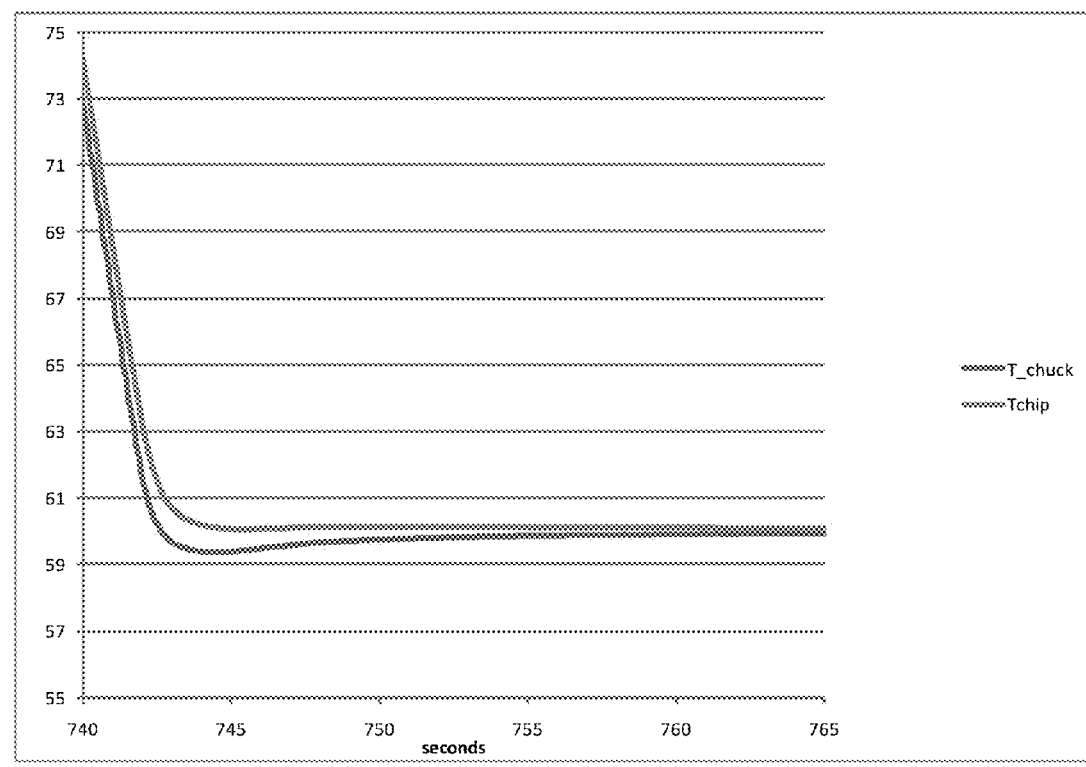
FIG. 8B is a simplified plot showing the temperature of the thermal chuck and the microfluidic device as a function of time during cooling according to an embodiment of the present invention.

FIG. 8B is a simplified plot showing the temperature of the thermal chuck and the microfluidic device as a function of time during cooling according to an embodiment of the present invention. As with the heating process, the temperature drop of the thermal chuck leads the temperature drop of the microfluidic device slightly. Additionally, the temperature of the chuck decreases and stabilizes with little undershoot. The ramp rate of the microfluidic device temperature is on the order of 5.5° C./s from 95° C. to 60° C.

Figure 9:
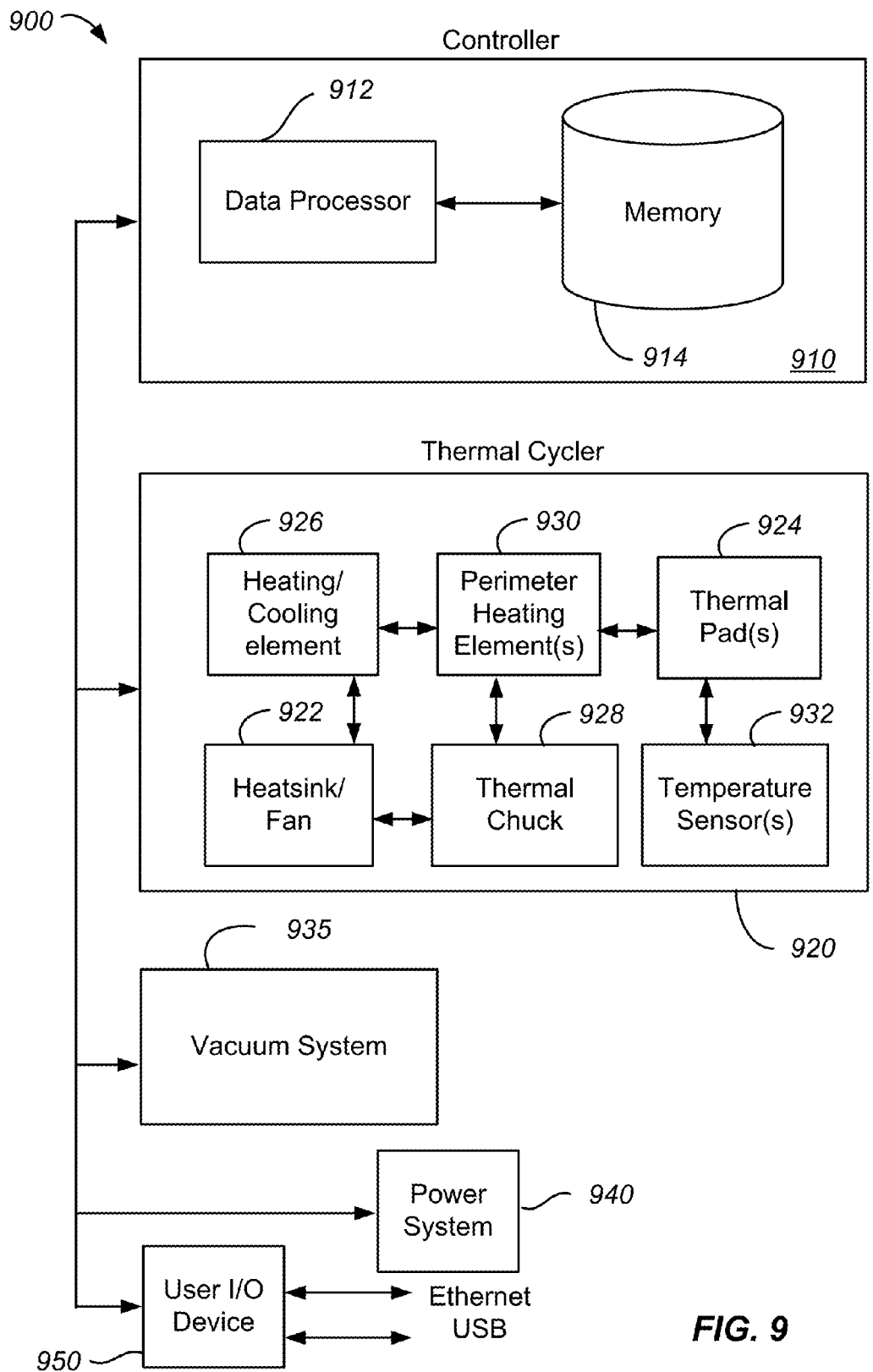
FIG. 9 is a simplified schematic diagram of a thermal cycler system according to an embodiment of the present invention.

FIG. 9 is a simplified schematic diagram of a thermal cycler system according to an embodiment of the present invention. The thermal cycler system 900 includes a controller 910, which includes a data processor 912 (also referred to as a processor), and a memory 914. The data processor 912 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the present invention in software, firmware and/or hardware. As an example, such processors include dedicated circuitry, ASICs, combinatorial logic, other programmable processors, combinations thereof, and the like.

The memory (also referred to as a database or a computer readable medium) 914 can be local or distributed as appropriate to the particular application. The memory can store information related to the operation of the thermal cycling system, program code and instructions executed by the data processor 912, and other suitable data.

Memory 914 may include a number of memories including a main random access memory (RAM) for storage of instructions and data during program execution and a read only memory (ROM) in which fixed instructions are stored. Thus, memory 914 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

Although the controller 910 is illustrated as a single component in FIG. 9, this is not required by embodiments of the present invention. In some embodiments, multiple boards are utilized to perform the functions of the controller. For example, a first driver board could be used to control the vacuum pump used to provide vacuum to a vacuum chuck acting as the thermal chuck, a valve to actuate the vacuum, a fan attached to the heatsink, and the like. A second board could perform functions associated with the control loop illustrated in FIG. 6A. A third board could be used to control the user I/O device 950. Thus, although a single controller 910 is illustrated in FIG. 9, the functions of the controller can be performed by multiple sub-controllers. The multiple sub-controllers can be in communication with each other as appropriate to the particular application. One of ordinary skill in the art would recognize many variations, modifications, and alternatives.

The thermal cycler system 920 includes the heatsink 922, one or more thermal pads 924, a heating/cooling element 926, the thermal chuck 928, perimeter heaters 930. The thermal cycler system 920 may also include a retaining ring or other attachment mechanism. Temperature sensors (932) are used to monitor the temperature of the thermal chuck, the heatsink, and other elements of the thermal cycler system as appropriate to the particular application.

The thermal cycler system 900 also includes a power system 940 (e.g., 100-240 V AC power). Depending on the voltages utilized by the various control boards, the AC power signal may be converted to a DC signal (e.g., 24 V DC) to provide a suitable power supply to the control boards discussed in relation to controller 910. The thermal cycler system 900 further includes a vacuum system 935 including one more vacuum pumps. The vacuum system 935 can include one or more valves under the control of the controller 910 to actuate and deactuate vacuum as needed for the thermal cycler 920. The thermal cycler system 900 further includes a user input/output device 950, which may be connected to the Internet through an Ethernet or other suitable connection and access memory or other system resources through a USB or other suitable interface.

Figure 10A:
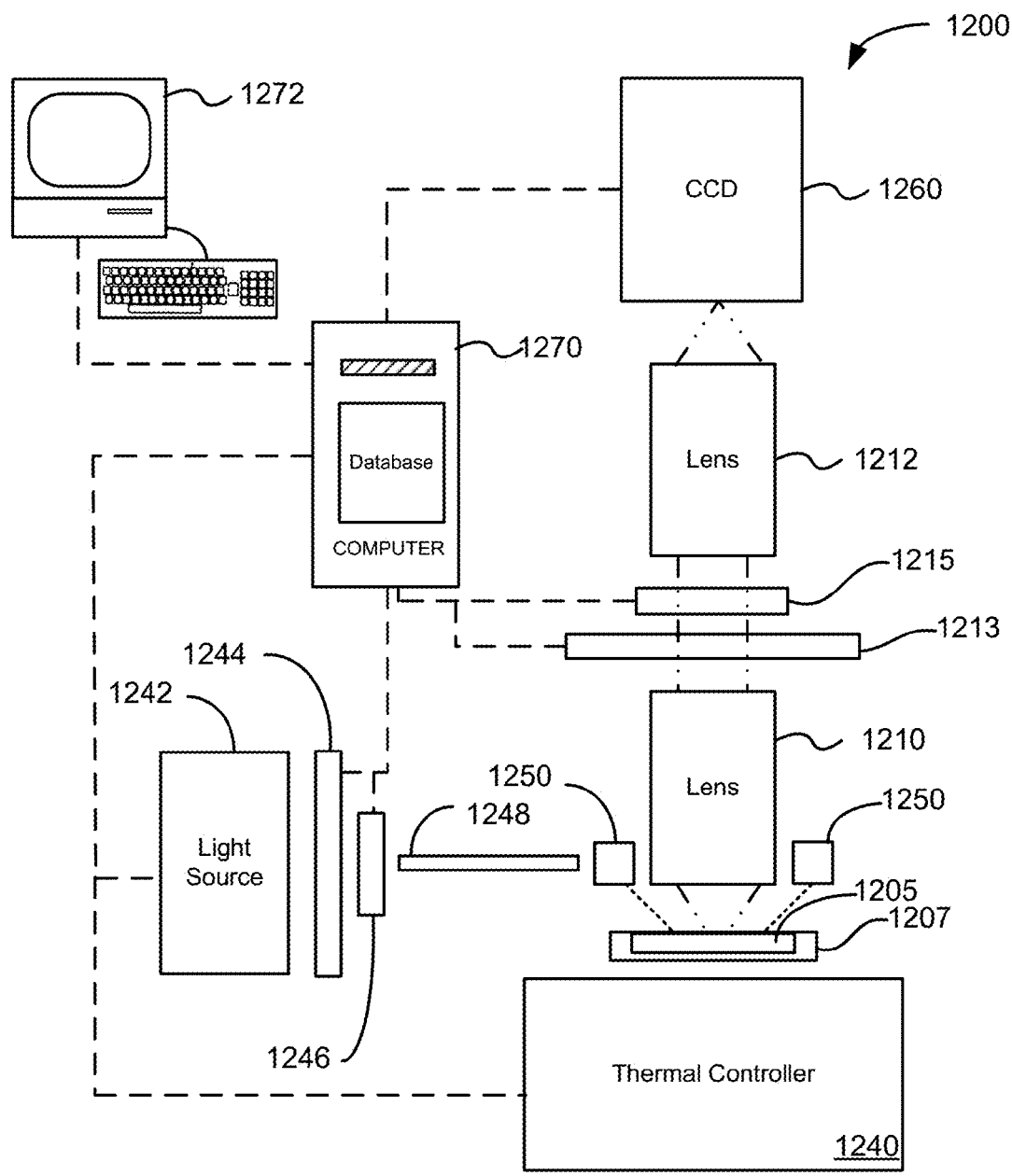
FIG. 10A is a simplified schematic diagram of a genotyping system including a thermal cycler according to an embodiment of the present invention.

FIG. 10A is a simplified schematic diagram of a genotyping system including a thermal cycler according to an embodiment of the present invention. As illustrated in FIG. 10A, an optical source 1242 is provided according to embodiments of the present invention. As will be described more fully below, in some embodiments of the present invention, light from optical source 1242 is utilized to induce fluorescence in a sample. In other embodiments, chemiluminescence is utilized as a indicator. Depending on the embodiment, system components will be added, removed, or used, as will be evident to one of skill in the art. In various embodiments, optical sources including light emitting diodes (LEDs), lasers, arc lamps, incandescent lamps, and the like are utilized. These sources may be polychromatic or monochromatic. In a particular embodiment, the optical source is characterized by a first spectral bandwidth. In a specific embodiment, the optical source is a white light source producing optical radiation over a spectral range from about 400 nm to about 700 nm. Merely by way of example, a Lambda LS 300W Xenon Arc lamp, available from Sutter Instruments of Novato, Calif. is utilized as an optical source is some embodiments of the present invention. As will be evident to one of skill in the art, other optical sources characterized by larger or smaller spectral bandwidths are capable of being utilized in alternative embodiments.

Excitation filter wheel 1244 is illustrated in FIG. 10A. In some embodiments, for example, those in which the optical source is polychromatic, the excitation filter wheel 1244 is utilized to spectrally filter the light emitted by the optical source 1242. Of course, multiple filters could also be used. As an example, in an embodiment, the excitation filter wheel provides a number of spectral filters each adapted to pass a predetermined wavelength range as appropriate for exciting specific fluorescence from a sample. As illustrated in FIG. 10A, the excitation filter wheel 1244 is coupled to computer 1270, providing for computer control of the filters. In a particular embodiment, the excitation filter wheel provides a number of spectral filters:

Filter 1: A filter with a center wavelength of 485 nm and a spectral bandwidth of 20 nm;

Filter 2: A filter with a center wavelength of 530 nm and a spectral bandwidth of 20 nm; and Filter 3: A filter with a center wavelength of 580 nm and a spectral bandwidth of 20 nm.

As will be evident to one of skill in the art, embodiments of the present invention are not limited to these particular spectral filters, but will utilize spectral filters adapted for fluorescence processes for particular samples. Moreover, although the previous discussion related to the use of a filter wheel, this is not required by the present invention. In alternative embodiments, spectral filters are provided in geometries other than a wheel. For example, spectral filters that drop into a filter holder, electro-optic filters, filters placed into the optical path by actuators, and the like are included according to embodiments of the present invention. Moreover, in other embodiments, the optical source is a tunable laser adapted to emit radiation at predetermined wavelengths suitable for excitation of fluorescence. One of ordinary skill in the art would recognize many variations, modifications, and alternatives.

As illustrated in FIG. 10A, excitation shutter 1246 is provided according to embodiments of the present invention. The excitation shutter is operated under control of a computer 1270 in some embodiments, to block/pass the optical signal generated by the optical source 1242 and spectrally filtered by the excitation filter wheel 1244. Depending on the application, the excitation source is blocked while samples are inserted and removed from the system as well as for calibration operations. In some embodiments, the excitation shutter is not utilized, for example, in embodiments utilizing laser sources, which provide alternative means to extinguish the optical source.

When the excitation shutter is operated in an open position, the optical excitation signal passes through a fiber bundle 1248 and is directed so as to impinge on a microfluidic device 1205 provided in chip carrier to a seven. Other embodiments of the present invention utilize quartz light guides, liquid light guides, other scrambling systems, and the like to increase illumination homogeneity. As illustrated in FIG. 10A, the excitation optical signal is directed, through reflection by optical illuminator 1250, refraction, or combinations thereof, to impinge on a surface of the microfluidic device 1205. As illustrated in FIG. 10A, illumination of the microfluidic device is via optical illuminator 1250. In other embodiments illumination maybe coupled to the microfluidic device obliquely from one or more sides of device, via a ring light, or via a portion of the collection optical train (the optical path between the microfluidic device and the detector 1260.

In some embodiments, the illumination of the microfluidic device with light produced by the excitation source is provided over a two-dimensional area of the sample. In these embodiments, a large field of view is provided, which enables the performance of fluorescence applications that involve imaging of time resolved chemical processes and reactions. As an example, fluorescent imaging of protein calorimetry and nucleic acid amplification processes are time resolved processes that benefit from embodiments of the present invention. In some of these processes, simultaneously excitation of the fluorescent samples provided in a number of reaction chambers and simultaneous collection of the fluorescent signals produced by the reactions occurring in the number of reaction chambers is desirable. In other processes, for instance, fluorescence lifetime imaging, a brief excitation pulse is followed by detection (and analysis) of the fluorescent signal as it decays in time from an initial level. One of ordinary skill in the art would recognize many variations, modifications, and alternatives.

As an example, nucleic acid amplification processes typically include the target DNA, a thermostable DNA polymerase, two oligonucleotide primers, deoxynucleotide triphosphates (dNTPs), a reaction buffer, and magnesium. Once assembled, the reaction is placed in a thermal cycler, an instrument that subjects the reaction to a series of different temperatures for varying amounts of time. This series of temperature and time adjustments is referred to as one cycle of amplification. Each cycle theoretically doubles the amount of targeted sequence (amplicon) in the reaction. Ten cycles theoretically multiply the amplicon by a factor of about one thousand; 20 cycles, by a factor of more than a million in a matter of hours. In some applications, it is desirable to acquire fluorescent imaging data from a large area (e.g., on the order of several $cm^2$) in a time period ranging from seconds to minutes.

In some embodiments of the present invention, the methods and systems provided by embodiments of the present invention facilitate image capture processes that are performed in a predetermined time period. Merely by way of example, in an embodiment of the present invention a method of imaging microfluidic devices is provided. The method includes capturing an image of a spatial region associated with at least a determined number of chambers of a microfluidic device using an image detection spatial region during a time frame of less than one minute, whereupon the capturing of the image of the spatial region is substantially free from a stitching and/or scanning process.

Embodiments of the present invention provide a variety of time frames for image capture, ranging from 1 millisecond to 1 minute. In some embodiments, time frames for image capture are greater than one minute. Depending on the emission properties associated with the processes performed in the chambers of the microfluidic device, the time frame for image capture will vary. For example, in an embodiment, the time frame is 10 ms, 50 ms, 100 ms, 250 ms, 500 ms, 750 ms, or 1 second. In other embodiments, the time frame is 2 seconds, 5 seconds, 10 seconds, 15 seconds, 20 seconds, 30 seconds, 40 seconds, 50 seconds, or 1 minute. Of course, the time frame will depend on the particular applications.

In some embodiments, the image capture process is performed in a synchronous manner, capturing an image of a determined number of chambers simultaneously. As an example, in an exemplary PCR process, the microfluidic device is maintained at a temperature of 92° C. for a time period of 15 seconds. Subsequently, the microfluidic device is maintained at a temperature of 60° C. for 60 seconds. The heating and cooling cycle is repeated at a one minute cycle period for a number of cycles. Utilizing embodiments of the present invention, images of a determined number of chambers present in the microfluidic device are acquired synchronously, while the chambers are maintained at a uniform temperate as a function of position. For example, a two-dimensional image of an entire microfluidic device may be acquired utilizing a 30 second exposure while the microfluidic device is maintained at the temperature of 60° C. One of skill in the art will appreciate the benefits provided by the present invention over raster scanning or stitching systems, in which images of chambers in a first portion (e.g., an upper left quadrant) of the microfluidic device are acquired prior to images of chambers in a second portion (e.g., a lower right quadrant) of the microfluidic device.

In other embodiments, multiple images are acquired of the determined number of chambers during a time frame of less than one minute. As an example of these embodiments, multiple images associated with multiple fluorophores are acquired in a particular embodiment. During the 60 second time period during which the microfluidic device is maintained at the temperature of 60° C., three consecutive images utilizing exposures of 20 seconds may be acquired for three different fluorophores, for example, Rox™, Vic®, and Fam™. Of course, depending on the application, the exposure times may be shorter, even as short as a second or less. Utilizing these multiple images, differential fluorescence ratios can be calculated and analyzed. Of course, depending on the strength of the fluorescent emissions, the exposure times for the various fluorophores may be modified as appropriate the particular application. In this way, embodiments of the present invention provide for imaging of a microfluidic device in multiple spectral bands while the microfluidic device is maintained a constant temperature. The constant temperature, as illustrated by the previous example, may be a portion of a PCR process including cyclical temperature processes.

Embodiments of the present invention provide methods and systems are also adapted to perform and analyze chemiluminescence processes. In some of these processes, reactions occur on a first time scale and an image of the chemiluminescence process is acquired on a second time scale. In a particular process, the second time scale is less than the first time scale. Thus, embodiments of the present invention are adapted to capture synchronous images of chemiluminescence processes when the samples in the reaction chambers of interest have been reacting for an equal amount of time. In some of these processes, temperature control, including temperature cycling of the samples is provided, whereas in other embodiments, the reaction chambers are maintained at a constant temperature.

As illustrated in FIG. 10A, a thermal controller, also referred to as a temperature controller, 1240 is provided according to embodiments of the present invention. A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in a matrix of channels of a microfluidic device).

In some embodiments, the microfluidic device is contacted with a thermal control device such that the thermal control device is in thermal communication with the thermal control source so that a temperature of the reaction in at least one of the reaction chamber is changed as a result of a change in temperature of the thermal control source. In different embodiments, the thermal transfer device may comprise a semiconductor, such as silicon, may comprise a reflective material, and/or may comprise a metal.

The thermal control device may be adapted to apply a force to the thermal transfer device to urge the thermal transfer device towards the thermal control source. The force may comprise a mechanical pressure, a magnetic force, an electrostatic force, or a vacuum force in different embodiments. For example, in one embodiment, the force comprises a vacuum force applied towards the thermal transfer device through channels formed in a surface of the thermal control device or the thermal transfer device. A level of vacuum achieved between the surface of the thermal control device and a surface (or a portion of a surface) of the thermal transfer device may be detected. Such detection may be performed with a vacuum level detector located at a position along the channel or channels distal from a location of a source of vacuum. When the vacuum does not exceed a preset level, an alert may be manifested or a realignment protocol may be engaged.

The array device may be contacted with the thermal control device by employment of one or more mechanical or electromechanical positioning devices. Carrying out of the method may be automatically controlled and monitored. For example, such automatic control and monitoring may be performed with an automatic control system in operable communication with a robotic control system for introducing and removing the array device from the thermal control device. The progress of the reactions may also be monitored.

A unit may be provided comprising the thermal control device. A system may be provided comprising the array device and the thermal control device. To ensure the accuracy of thermal cycling steps, in certain devices it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself.

Imaging system 1200 operates, in one embodiment, in the following manner. First, microfluidic device 1205 is securely placed on carrier 1207. Based on a fixed feature of the microfluidic device 1205, for example, an edge of the base support of microfluidic device, computer 1270 then causes and x,y drive (not shown) to move the carrier 1207 to align the microfluidic device in a first x,y position. In some embodiments, one or more fiducial markings are utilized during the alignment and positioning process. In a specific embodiment, a user of the system then registers the precise coordinate of one or more fiducial marks with the imaging system. In other embodiments, this process is performed automatically as the centroids of the fiducials can be calculated precisely by locating a symmetric XY fiducial object and removing any non-symmetric components. In some embodiments, features of the fiducials, such as edges and corners are utilized during alignment processes. One of ordinary skill in the art would recognize many variations, modifications, and alternatives.

Under the control of computer 1270, either adjustments of the carrier 1207 to position it in the focal plane of the optical elements 1210 and 1212 or adjustments of the optical elements 1210 and 1212 to position the focal plane of the optical elements 1210 and 212 to the carrier 1207 are performed. In preferred embodiments, the field of view can embrace an entire microfluidic device, including the number of reaction chambers present on the microfluidic device.

A fluorescent, chemiluminescent, or optical signal emitted by the chemical processes occurring in the reaction chambers of the microfluidic device is collected by a first lens system 1210. In some embodiments of the present invention, the first lens system is a multi-element optical train including one or more lenses and one or more apertures. The optical properties of the first lens system 1210 including focal length, f/#, and the like are selected to provide desired optical performance. One of ordinary skill in the art would recognize many variations, modifications, and alternatives. An emission shutter 1215 is illustrated in FIG. 10A to provide for blocking of light rays propagating more than a predetermined distance from the optical axis, although this is not required by the present invention.

Referring once again to FIG. 10A, an optical filter device 1213 is provided as part of the optical assembly. In some embodiments, the optical filter device is a filter wheel 1213 comprising a number of optical elements adapted for passing and optically processing fluorescent or chemiluminescent emissions produced by fluorescently or chemiluminescently labeled reagents. As an example, in an embodiment, a first section of the emission filter wheel is adapted to pass fluorescent emissions produced by a first fluorescent dye, for example, Cy™3 Fluor, available from Amersham Biosciences, part of GE Healthcare of Piscataway, N.J. A second section of the emission filter wheel is adapted to pass fluorescent emissions produced by a second fluorescent dye, for example, Cy™5 Fluor also available from Amersham Biosciences. Of course, the use of these fluorescent dyes is not required by the present invention. In alternative embodiments, Alexa Fluors, available from Invitrogen Corporation of Carlsbad, Calif., are utilized. As an example, in another embodiment, a first section of the emission filter wheel is adapted to pass fluorescent emissions produced by a third fluorescent dye, for example, Alexa Fluor 350, available from Invitrogen Corporation. A second section of the emission filter wheel is adapted to pass fluorescent emissions produced by a fourth fluorescent dye, for example, Alexa Fluor 488, also available from Invitrogen Corporation. Additional details related to the emission filter wheel will be provided below.

In some embodiments, the optical filter device 1213 and the emission shutter 1215 are located between the first lens system and the second lens system. In some of these embodiments, light rays passing through the optical filter device propagate at small angles with respect to the optic axis. As will be evident to one of skill in the art, spectral filters (e.g., interference filters) placed in regions with small incident ray angle are simpler to design and can potentially provide narrower total spectral bandwidth, through such narrow spectral bandwidth characteristics and/or filter positioning are required by the present invention. As illustrated in FIG. 10A, both the optical filter device and the emission shutter are coupled to computer 1270, providing for computer control of these elements. Moreover as will be evident to one of skill in the art, multiple, and possibly multiple identical filters, may be provided in the optical path to increase the blockage of excitation wavelengths. In some embodiments these filters are angled with respect to the optic axis so that light rays reflected off of the filters walk out of the optical path.

In other embodiments, certain intercalation dyes that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

An second lens system 1212 is also illustrated in FIG. 10A. Fluorescent or chemiluminescent emission passing through the optical filter device 1213 and the emission shutter 1215 is focused by the second lens system onto a detector 1260. In an embodiment, the detector is a CCD camera array, but this is not required by the present invention. In a particular embodiment, an array detector, approximately the size of the microfluidic device, is utilized. Preferably, the pixel size of the detector array 1260 is selected to provide an area smaller than the area of the reaction chambers in the microfluidic device, thereby providing multiple detector pixels per reaction chamber. In a particular embodiment, the detector 1260 is a CCD array with approximately 15 µm×15 µm pixels.

A number of different detection strategies can be utilized with the microfluidic devices that are provided herein. Selection of the appropriate system is informed in part on the type of event and/or agent being detected. The detectors can be designed to detect a number of different signal types including, but not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates.

Illustrative detection methodologies suitable for use with the present microfluidic devices include, but are not limited to, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization anisotropy, fluorescence lifetime, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

In some embodiments, detection occurs at a "detection section," or "detection region." These terms and other related terms refer to the portion of the microfluidic device at which detection occurs. In some microfluidic devices, the detection section is generally the reaction chambers present in the microfluidic device. The detection section for other devices may be within regions of flow channels that are adjacent an intersection, the intersection itself, or a region that encompasses the intersection and a surrounding region.

The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by one ore more optical detectors. The optical detector can include one or more photodiodes (e.g., avalanche photodiodes), a fiber-optic light guide leading, for example, to a photomultiplier tube or tubes, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

External detectors are usable because the devices that are provided are completely or largely manufactured of materials that are optically transparent at the wavelength being monitored. This feature enables the devices described herein to utilize a number of optical detection systems that are not possible with conventional silicon-based microfluidic devices.

A particular embodiment of the present invention utilizes a detector in the form of a CCD camera and an optical path that provides for a large field of view and a high numerical aperture to maximize the amount of light collected from each reaction chamber, thereby increasing detection sensitivity. In this embodiment, the CCD is used as an array of photodetectors wherein each pixel or group of pixels corresponds to a reaction chamber rather than being used to produce an image of the array. Thus, the optics may be designed or altered such that image quality is reduced or the image is blurred at the detector in order to increase the useable depth of field of the optical system to collect more light from each reaction chamber. Particularly because the assays contemplated in some embodiments of the present invention include biological assays using fluorescent dyes, which dyes photobleach due to exposure to excitation light hence limiting the total number of signal photons obtainable from a given sample, efficient collection of the limited signal photons can be of importance in instruments such as that discussed. Etendue considerations relate the object and image NA (numerical aperture) and total system magnification for any optical system; since image-side NA can be limited (e.g. by reflection losses at the CCD surface for high-incident-angle rays), in general, arbitrarily high object (sample)-side NA is not achievable simultaneously with arbitrary system magnification. In fact, a larger system magnification can allow a higher object-side NA without requiring a simultaneous (and potentially deleterious for reasons described above) rise in image-side NA. Consequently, in the system described, a large CCD (e.g., 30.7 mm×30.7 mm) focal-plane array has been used to allow for a 1:1 optical system (i.e., a system magnification of 1). This allows a collection NA of 0.36 simultaneous with an image-side NA of 0.36 onto the CCD, which provides reasonable performance with respect to surface reflection losses.

In some embodiments, larger object-side NAs result in reduced object-side depth-of-focus, and hence larger blurring at the detector (assuming blur due to depth of focus greater than or equal to blur due to lens aberrations and other issues) for a given depth of reaction chamber in the sample, limiting the allowable minimum spacing between reaction chambers at the sample if low crosstalk in signal between chambers is to be achieved. In conjunction with a 1:1 optical system, this object-side NA consideration is in good keeping with the ~0.5 NA maximum generally desirable NA onto a CCD (or silicon detector) if one is to avoid reflection losses at the surface thereof. The 1:1 imaging lens system is furthermore inherently free of most odd-order aberrations, increasing the advantage of this particular magnification (M=1). The use of a 1:1 optical system with a detector as large or larger than the microfluidic system to be imaged is thus provided by some embodiments of the present invention as a design for the detailed system.

In other embodiments, there may be a cost constraint related to the size of the detector (e.g. a CCD focal-plane array). For example, some current high quantum-efficiency, full-frame CCD arrays have dimensions of 27.6 mm×27.6 mm. This detector is slightly smaller than a microfluidic device with dimensions of 30.7 mm×30.7 mm, resulting in a system magnification of 0.88 as a design for the system described. Being near system magnification M=1, constraints related to the detector (image-side) incident NA described above are satisfied for such a magnification.

In other embodiments, a given XY-plane (perpendicular to the optical axis) spacing and size of the reaction chambers may be specified (e.g. to achieve a desired density of sample-chambers in the XY-plane), while constraints on the minimum total volume of the chambers remain (e.g. to achieve minimum required chemical volumes, for instance to avoid over-large statistical fluctuations due to small numbers of reagent or target molecules, or simply to achieve a required minimum number of fluorescent or otherwise optically-emitting molecules or objects). In such a case, it may be necessary to extend the chambers parallel to the Z (optical)-axis such that the total volume of each chamber remains equal to or greater than some minimum figure. Greater extension along Z (creating high-aspect ratio, or columnar chambers which concentrate the sample to be interrogated along the Z-axis) will generally result in a larger blur of the chamber image at the detector for given object-side NA, due to depth-of-focus considerations, assuming blur due to depth of focus is greater than or equal to blur due to lens aberrations and other issues. In some situations, this will lead to the user of a lower object-side NA. Use of a lower NA lens system allows for greater depth of focus and hence light collection from a chambers extended parallel to the optic axis without generally incurring inordinate crosstalk in the optical signal between adjacent or nearby chambers. In this way, a greater density of chambers in the X-Y plane (the place perpendicular to the optic axis) may be used without inordinate crosstalk, while the total chamber volume may be kept large by extension of the chambers in Z (parallel to the optic axis). In this case, or other cases where a lower object-side NA is acceptable (e.g., cases where a larger XY spacing of reaction chambers allows for more chamber-image blur at the detector without undue crosstalk; in non-light-limited applications, where higher NA is not essential; where there is sufficient sample that photobleaching is not an issue; non-photobleaching samples, circumstances such as lower acceptable system sensitivity), a lower system magnification (M<1) may be suitable, particularly if $M \geq NA_o/0.5$, or more preferably $M \geq NA_o/0.36$, where $NA_o$=object side NA, or more generally $M \geq NA_o/NA_{det}$ where $NA_{det}$=maximum NA allowable onto the detector face without overlarge reflection/insertion losses to the detector ($NA_{det}$=0.36 to 0.5 for a typical CCD).

In cases where object-side depth-of-focus and/or blur requirements do not necessitate an object-side NA≤0.36, or possibly 0.5, or more generally $NA_o \leq NA_{det}$, a larger detector is desirable since due to Etendue considerations (as discussed above), since a larger M (generally requiring a larger detector for a given sample size) will allow a smaller $NA_i$ (image-side NA) for a given $NA_o$. Hence where light-collection requirements (e.g. to achieve a certain assay sensitivity) call for a large $NA_o$ (defined by $NA_o > NA_{det}$) and depth-of-focus and other design considerations (e.g. cost) allow for a large $NA_o$, a larger M is desirable such that losses are minimized at the detector. In such embodiments it can be useful to use a detector device, for example, one or more CCD devices, having a size of, or larger than, the area of the microfluidic device to be imaged. Use of such a large detector allows an increase in the magnification of the optical system, and hence (via etendue considerations) higher NA light collection from the sample for a fixed incident NA onto the detector (the latter set, e.g., by reflection losses at the CCD surface at high incoming ray incident angles).

A particularly preferred detector uses a CCD camera and an optical path that provides for a large field of view and a high numerical aperture to maximize the amount of light collected from each reaction chamber, thereby increasing detection sensitivity. In this regard, the CCD is used as an array of photodetectors wherein each pixel or group of pixels corresponds to a reaction chamber rather than being used to produce an image of the array. Thus, the optics may be altered such that image quality is reduced or defocused to increase the depth of field of the optical system to collect more light from each reaction chamber. In some embodiments, it is useful to employ high aspect ratio, or columnar chambers, to concentrate the sample to be interrogated by the detector along the optical axis of the optical system, and preferably by defocussing the image to increase the depth of field. Use of a low NA lens system, preferably a bilaterally symmetrical lens system is used. It is also useful to use a detector device, for example, one or more CCD devices, having a size of, or larger than, the area of the microfluidic device to be imaged. Used in conjunction with the low NA optics, improved detection sensitivity can be realized.

A detector system can include a light source for stimulating a reporter that generates a detectable signal. The type of light source utilized depends in part on the nature of the reporter being activated. Suitable light sources include, but are not limited to, lasers, laser diodes, white light sources, and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

Certain intercalation dyes that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

As illustrated in FIG. 10A, some embodiments of the present invention provide a 1:1 imaging system adapted to generate and detect fluorescent, chemiluminescent, bioluminescent, and other signals from the microfluidic device. A 1:1 imaging system is provided in some embodiments that utilizes an image detection device as large as the sample to be imaged. By providing 1:1 imaging of a large field of view, on the order of several $cm^2$, embodiments of the present invention provide increased numerical aperture (NA) optical systems. Because light collection efficiency is approximately proportional to $NA^2$, the increase in NA provided by some embodiments of the present invention enable the collection of suitable fluorescent signals from reaction chambers comprising reaction volumes on the order of one to tens of nanoliters and active fluorophore concentrations on the order of 1.0 nanoMolar. In other embodiments, active fluorophore concentrations in picoMolar ranges provide suitable fluorescent signals.

Additionally, embodiments of the present invention provide for imaging systems that are slightly reducing, forming, for example, an image that ranges from about the same size as the object to about half the object size. For example, in an embodiment, an image of a spatial region of a microfluidic device is transmitted and captured, the spatial region being associated with more than 96 chambers. An image detecting device is used to capture the image of the spatial region using an image detection spatial region that is about equal to or slightly less in size than the spatial region of the microfluidic device. Merely by way of example, the ratio of the area of the spatial region of the microfluidic device to the area of the image of the spatial region can be 1:1, 1:0.99, 1:0.95, 1:0.9, 1:0.88, 1:0.85, 1:0.8. 1:0.7, 1:0.6, and 1:0.5. In some embodiments, the ratio is less than 1:0.5. These particular ratios are merely exemplary, as the ratio selected for the imaging system will depend on the particular application.

In some embodiments, the optical imaging system includes a field of view of about 3 cm×3 cm. In other embodiments, the optical imaging system includes a field of view that ranges from about 1 cm×1 cm to about 5 cm×5 cm. In particular embodiments, an object field of view of 2 cm×2 cm, 2.5 cm×2.5 cm, 2.76 cm×2.76 cm, 3.07 cm×3.07 cm, 3.5 cm×3.5 cm, and 4 cm×4 cm, is provided. In general, the field of view of the optical imaging system is selected to correspond to the spatial region of the microfluidic device, for example, an area including a number of reaction chambers of interest.

Moreover, embodiments of the present invention provide optical imaging systems with a range of numerical apertures. As an example, an NA ranging from 0.1 to 0.5 is provided according to various embodiments. In a particular embodiment, NAs of 0.15, 0.18, 0.2, 0.23, 0.25, 0.3, 0.36, and 0.4 are provided.

The spatial resolution of the optical imaging system will generally be a function of the size of the pixels in the image detecting device. In some embodiments of the present invention, the magnification (equal to one for some embodiments) and the size of the pixels present in the detector will determine the number of pixels associated with each reaction chamber. Generally, it is preferable to have multiple detector pixels associated with each reaction chamber. For example, if a reaction chamber is 45 μm on a side, up to nine square pixels having a side dimension equal to 15 μm will overlap with the reaction chamber in the 1:1 imaging system. Thus, according to embodiments of the present invention, the number of pixels associated with each reaction chamber ranges from 1 to 100. For example, 4 pixel regions, 9 pixel regions, 16 pixel regions, 25 pixel regions, 36 pixel regions, 49 pixel regions, 64 pixel regions, and 81 pixel regions are associated with each reaction chamber according to some embodiments of the present invention.

In embodiments of the present invention, a range of pixel sizes from 1 $\mu m^2$ to 900 $\mu m^2$ are utilized. For example, square pixels 1 μm on a side, 2 μm on a side, 3 μm on a side, 4 μm on a side, 5 μm on a side, 10 μm on a side, 13.5 μm on a side, 15 μm on a side, 20 μm on a side, 25 m on a side, and 30 μm on a side are utilized in various embodiments of the present invention. As will be evident to one of skill in the art, the pixel size, the detector array dimensions, and the number of pixels per array are related. In alternative embodiments, rectangular pixels with pixel areas ranging from 1 $\mu m^2$ to 900 $\mu m^2$ are utilized.

Moreover, detector arrays, also referred to as image detecting devices, including a range of pixel counts are utilized according to various embodiments of the present invention. Array dimensions range from 512×512 pixel regions to 3,000×3,000 pixel regions. Depending on the availability of detector arrays, greater numbers of pixels per array may be provided in some embodiments. In particular embodiments, array dimensions of 1,024×1,024 pixel regions and 2,048 by 2,048 pixel regions are utilized.

Embodiments of the present invention provide an optical imaging system characterized by several system parameters. For example, a working distance of greater than 35 mm, for instance, 45.92 mm is available through embodiments of the present invention. In another embodiment, a Root-Mean-Square (RMS) spot diameter averaging 13.44 μm with a maximum value of 17.85 μm is provided. Moreover, through embodiments of the present invention, an illumination variation of about ±5% is achieved. In some embodiments, the overall length of the optical imaging system is 542.1 mm with a maximum filter AOI of 12.56 degrees, a maximum beam diameter at the filter of 76 mm, a distortion of <0.10%, and a maximum lens diameter of 5.512 inches.

As illustrated in FIG. 10A, optical imaging systems provided according to some embodiments of the present invention include fluorescence imaging systems coupled to thermal control modules. Such systems are adapted to collect data from microfluidic chips with N×M geometries. In some embodiments, N is equal to M. For example, embodiments of the present invention utilize microfluidic devices with 48×48 reaction chambers, 96×96 reaction chambers, and other geometries. In a particular embodiment, 96 samples and 96 reagents are utilized in a microfluidic device with a 96×96 reaction chamber geometry. As will be evident to one of skill in the art, the methods and systems provided according to embodiments of the present invention enable one platform to perform multiple applications.

Figure 10B:
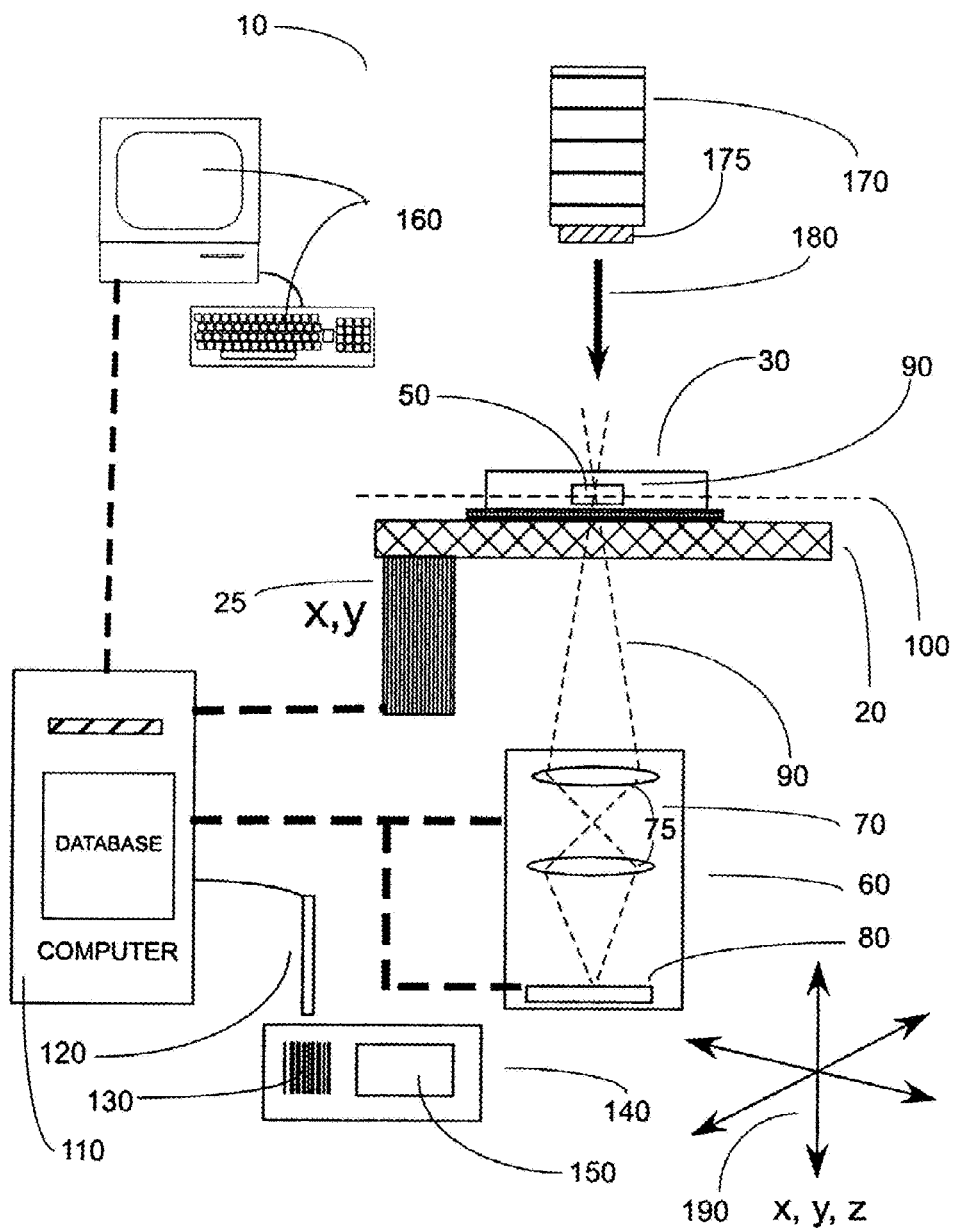
FIG. 10B depicts an overview of an exemplary genotyping system according to an alternative embodiment of the present invention.

FIG. 10B depicts an overview of an exemplary genotyping system according to an alternative embodiment of the present invention. In some embodiments, the imaging system illustrated in FIG. 10B is utilized for imaging of microfluidic devices including devices adapted to perform protein crystallization processes. Additional details regarding imaging systems as illustrated in FIG. 10B and associated microfluidic devices are found in co-pending and commonly owned U.S. patent application Ser. No. 10/902,494, filed Jul. 28, 2004 and U.S. patent application Ser. No. 10/851,777, filed May 20, 2004, the disclosures of which are incorporated by reference herein for all purposes. In particular, additional details regarding microfluidic devices provided according to embodiments of the present invention and their use in conjunction with the imaging system as shown in FIG. 10B are found therein. These diagrams are merely examples, which should not unduly limit the scope of the claims herein. One of ordinary skill in the art would recognize many variations, alternatives, and modifications.

Imaging system (10) operates, in one embodiment, in the following manner. First, microfluidic device (30) is securely placed on stage (20). Based on a fixed feature of the microfluidic device (30), for example, an edge of the base support of microfluidic device (30), computer (110) then causes x,y drive (25) to move stage (20) about to align microfluidic device (30) in a first x,y position with a first of a plurality of fiducial markings, wherein the fiducial markings are embedded within the microfluidic device at a known z dimension distance from a chamber center point, comes into focus by imaging device (60) based on dead reckoning from the fixed feature. A user of the system then registers the precise coordinate of the fiducial with the imaging system. Two or more additional fiducial marks are then likewise mapped with the assistance of a user. In other embodiments, this process is automatic as the centroids of the fiducials can be calculated precisely by locating the symmetric XY fiducial object and removing any non-symmetric components. Imaging device (60), under the control of computer (110) then adjusts the z dimension location of focal plane (100) to focus upon the fiducial marking. For example, once focused upon the first fiducial marking, the imaging system then obtains a first x,y coordinate image of microfluidic device (30) looking for additional fiducial markings within the field of view of imaging device (60). In preferred embodiments, the field of view can embrace an entire metering cell. The computer then analyzes the first x,y coordinate image to determine whether the microfluidic device has skew and stretch, and if skew or stretch are determined, transforms the first x,y image to align the image and coordinate map of the microfluidic device to an idealized coordinate map. The idealized coordinate map is used later during image subtraction and masking steps.

In preferred embodiments, with the microfluidic device x,y coordinate image aligned against the ideal coordinate map, the system then determines whether the stretch, distortion or lack of co-registration between the various microfluidic layers is present in the microfluidic device by comparing the location of the fiducial markings in the x,y coordinate image with the fiducial markings locations in the x,y coordinate image of the ideal stored image map. If differences are present between the actual fiducial locations and the imaged fiducial locations, a matrix transformation, preferably an Affine transformation, is performed to transform the imaged shape of the metering cell into a virtual shape of the ideal metering cell shape. By converting the actual image to a known and fixed ideal image using the matrix transformation computed from the differences between the measured actual fiducial locations and the stored ideal fiducial locations, image subtraction and other image analysis are made possible.

By computing the differences between the coordinate maps through matrix analysis, a matrix transformation may be developed to reform the actual image into an ideal image for use in further image processing described herein. By causing the imaged microfluidic device to conform to a standard shape, image subtraction and masking is possible to maximize the viewable area of a metering cell chamber. Moreover, if defects or debris are present within the chamber at time zero in a series of time based images, such defects or debris can be masked out of subsequent images to avoid false signals when applying automated analysis. In addition to masking off areas of the chambers which contain defects or debris, the walls of the chambers may be subtracted from subsequent images, again so as to not cause false readings in the subsequent analysis. The discrepancy between various layers, such as between the control layer and the channel layer, can also be calculated based on the position of a found object in the control layer, such as the control lines themselves. In another example, this correction is determined based on the control layer fiducials themselves. For certain embodiments, this extra transformation is important since the control layer partitions the protein chamber from the rest of the control line.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A thermal cycler for a microfluidic device, the thermal cycler comprising:
   a controller operable to provide a series of electrical signals;
   a heat sink comprising a plurality of radiator pins;
   a heating element in thermal communication with the heat sink and operable to receive the series of electrical signals from the controller, wherein the heating element comprises one or more of a central thermal electric cooler and one or more of a perimeter heater; and
   a thermal chuck in thermal communication with the heating element, wherein the thermal chuck comprises a heating surface operable to make thermal contact with the microfluidic device.

2. The thermal cycler of claim 1 the microfluidic device includes a plurality of reaction chambers.

3. The thermal cycler of claim 2 wherein the plurality of reaction chambers comprise 2,304 reaction chambers.

4. The thermal cycler of claim 3 wherein the plurality of reaction chambers comprise 9,216 reaction chambers.

5. A thermal cycler for a microfluidic device having a plurality of reaction chambers extending over a predetermined area in a lateral plane, the thermal cycler comprising:
   a controller operable to provide a series of electrical signals;
   a heat sink comprising a plurality of radiator pins;
   a heating element in thermal communication with the heat sink and operable to receive the series of electrical signals from the controller, wherein the heating element comprises one or more of a central thermal electric cooler and one or more of a perimeter heater; and
   a thermal chuck in thermal communication with the heating element, wherein the thermal chuck comprises a heating surface operable to make thermal contact with the microfluidic device wherein a temperature difference between a first portion of the heating surface supporting a first portion of the microfluidic device and a second portion of the heating surface supporting a second portion of the microfluidic device is less than 0.25° C.

6. The thermal cycler of claim 5 wherein the first portion of the microfluidic device and the second portion of the microfluidic device are separated by more than 40 mm in the lateral plane.

7. The thermal cycler of claim 6 wherein the first portion of the microfluidic device and the second portion of the microfluidic device are separated by more than 48 mm in the lateral plane.

8. The thermal cycler of claim 5 wherein the first portion of the microfluidic device is located at a first corner of the predetermined area and the second portion of the microfluidic device is located at a second corner of the predetermined area.

9. The thermal cycler of claim 5 wherein the plurality of reaction chambers comprise at least 500 reaction chambers.

10. The thermal cycler of claim 9 wherein the plurality of reaction chambers comprise 2,304 reaction chambers.

11. The thermal cycler of claim 9 wherein the plurality of reaction chambers comprise 9,216 reaction chambers.

12. The thermal cycler of claim 1 wherein the heating surface is characterized by a temperature ramp rate between 2.5 degrees Celsius per second and 5.5 degrees Celsius per second.

13. The thermal cycler of claim 1 wherein the heat sink further comprises a heat sink sensor.

14. The thermal cycler of claim 1 wherein the thermal cycler further comprises a first thermal pad positioned between the heat sink and the heating element.

15. The thermal cycler of claim 1 wherein the thermal cycler further comprises a second thermal pad positioned between the heating element and the thermal chuck.

16. The thermal cycler of claim 1 wherein at least one resistance temperature detector (RTD) is in thermal contact with the thermal chuck.

17. The thermal cycler of claim 5 wherein the heat sink further comprises a heat sink sensor.

18. The thermal cycler of claim 5 wherein the thermal cycler further comprises a first thermal pad positioned between the heat sink and the heating element.

19. The thermal cycler of claim 5 wherein the thermal cycler further comprises a second thermal pad positioned between the heating element and the thermal chuck.

20. The thermal cycler of claim 5 wherein at least one resistance temperature detector (RTD) is in thermal contact with the thermal chuck.

\* \* \* \* \*